(12) United States Patent
Valentine, Jr. et al.

(10) Patent No.: US 6,344,505 B1
(45) Date of Patent: Feb. 5, 2002

(54) MONO- AND BIS-BENZOTRIAZOLYLDIHYDROXYBIARYL UV ABSORBERS

(75) Inventors: Donald H. Valentine, Jr., Ridgefield, CT (US); John F. Stephen, Westchester, PA (US); Thomas P. Sassi, Stamford, CT (US)

(73) Assignee: Cytec Industries Inc., Stamford, CT (US)

( * ) Notice: Subject to any disclaimer, the term of this patent is extended or adjusted under 35 U.S.C. 154(b) by 0 days.

(21) Appl. No.: 09/438,754

(22) Filed: Nov. 11, 1999

(51) Int. Cl.[7] .................. C08K 5/34; C07D 249/18; C07D 249/20
(52) U.S. Cl. .................. 524/91; 548/260; 558/412; 558/413; 558/422; 568/707; 568/712; 568/718
(58) Field of Search .................. 548/260; 524/91; 568/718, 707, 712; 558/412, 413, 422

(56) References Cited

U.S. PATENT DOCUMENTS

| | | | | |
|---|---|---|---|---|
| 3,247,262 A | * | 4/1966 | Kaeding | 568/730 |
| 4,380,676 A | * | 4/1983 | Rasberger | 568/730 |
| 4,681,905 A | * | 7/1987 | Kubota et al. | 524/91 |
| 4,812,498 A | * | 3/1989 | Nakahara et al. | 524/91 |
| 4,859,726 A | * | 8/1989 | Wang et al. | 524/91 |
| 4,943,637 A | * | 7/1990 | Seino et al. | 568/260 |
| 5,187,289 A | * | 2/1993 | Fukuoka et al. | 548/260 |
| 5,922,882 A | * | 7/1999 | Mori et al. | 548/260 |
| 5,977,219 A | * | 11/1999 | Ravichandran et al. | 524/91 |
| 6,037,393 A | * | 3/2000 | Okumura et al. | 524/91 |
| 6,084,104 A | * | 7/2000 | Nakano et al. | 548/260 |

* cited by examiner

Primary Examiner—Veronica P. Hoke
(74) Attorney, Agent, or Firm—Pennie & Edmonds LLP

(57) ABSTRACT

Provided is a composition which contains a mono- or bis-benzotriazole compound, an N-oxide thereof, or a mixture of at least two of the preceding compounds. Representative bis-benzotriazole compounds include 3,3'-bis-(2H-benzotriazol-2-yl)-5,5'-di-tert-octyl-1,1'-biphenyl-2,2'-diols. Representative mono-benzotriazole compounds include 3-(2H-benzotriazol-2-yl)-5,5'-di-tert-octyl-1,1'-biphenyl-2,2'-diols. These mono- and bis-benzotriazole compounds are useful as stabilizers of degradable polymers against the degradative action of ultraviolet light. Also provided is a method of making these benzotriazole compounds by oxidative dimerization of the corresponding monomeric benzotriazole or by reductive cyclization of the corresponding azo- compound.

39 Claims, No Drawings

MONO- AND BIS-BENZOTRIAZOLYLDIHYDROXYBIARYL UV ABSORBERS

BACKGROUND OF THE INVENTION

1. Field of the Invention

This invention relates to mono-, bis-, and mixtures of mono- and bis-benzotriazolyldihydroxybiaryl compositions which are particularly useful as stabilizers for photodegradable polymers against the degradative action of ultraviolet (UV) light.

2. Description of Related Art

Stabilization of polymers by incorporation of ultraviolet light stabilizers in polymer films, coatings, fibers, and molded articles to provide protection against the degradative action of light, moisture, or oxygen has been an active area of research in recent years. Incorporation of a absorber into the degradable polymer has been one of the most widely used methods of stabilizing these polymers. Of the multitude of UV absorber compositions capable of providing stabilization, 2-(2-hydroxyaryl)benzotriazoles have generally been the most effective.

To perform its stabilizing role effectively, a stabilizer should have permanence within the photodegradable polymer. Without permanence, the degradable polymer would rapidly deteriorate when exposed to ultraviolet light. Many stabilizers suffer from high material losses during polymer processing caused by their relatively high volatility. They also suffer from the effects of material losses caused by poor retention within the polymer matrix after being incorporated into a degradable polymer. Poor retention, which is in general a consequence of the limited compatibility of the stabilizers with the polymer, may cause the stabilizer to migrate to the surface by a phenomenon generally referred to as "blooming." To compensate for the losses, the use of higher levels of the stabilizer may be. possible in some cases. The presence of high levels of stabilizers in a polymer, however, negatively impacts the physical properties of the polymer causing it to fail prematurely.

Attempts in the past to improve the permanence of stabilizers within the polymer matrix by increasing the molecular weight of the stabilizer have met with limited success.

For example, a successful attempt to oligomerize a suitable benzotriazole precursor to produce a high molecular weight material having reduced volatility has been described in U.S. Pat. No. 5,547,753. Other attempts to reduce volatility by converting benzotriazoles to higher molecular weight oligomers and polymers have generally resulted in a decreased retention of the stabilizers within the degradable polymer due to the incompatibility of the high molecular weight stabilizers with the degradable polymer to which they are added.

Increasing the molecular weight of a benzotriazole stabilizer by joining two benzotriazole compounds with an alkylene bridging group thereby decreasing volatility has been attempted. The preparation of alkylene or aralkylene bridged benzotriazoles are described in U.S. Pat. Nos. 5,237,071; 5,229,521; 4,937,348; 4,859,726; and Czechoslovakian Pat. No. 141,206 and some uses thereof are disclosed in U.S. Pat. Nos. 5,001,177; 4,812,498; 4,684,680; 4,684,679; 4,681,905; and 3,936,305. While bridged benzotriazole stabilizers have somewhat reduced volatility, their usefulness as stabilizers for degradable polymers has been limited because of their relative incompatibility.

Other attempts to increase the molecular weight of the stabilizer without introducing incompatibility by using an anchor group have been tried in the past without great success. For example, U.S. Pat. No. 4,319,016 describes the preparation of an ultraviolet light absorbing material from the reaction of a benzotriazole, formaldehyde, and melamine. It is stated therein that if the benzotriazole is present in amounts greater than 0.5 mole per mole of melamine, the compatibility of the resulting compound with a resin or solvent tends to be reduced. These compounds are sulfur containing benzotriazoles (i.e. thio-, sulfinyl-, and sulfonyl-substituted benzotriazoles) which have high molecular weight and low volatility. These benzotriazole stabilizers, however, have the disadvantage of being yellow, partly as a result of a shift of absorption to longer wavelengths and tailing into the visible spectrum. In addition, coatings and articles incorporating these sulfur containing benzotriazoles also exhibit an unacceptably high level of yellowness, particularly in clear coatings. This makes the sulfur containing benzotriazoles unsuitable for coatings applications.

U.S. Pat. Nos. 5,104,782, 5,294,530 and 5,360,692 contain a generic disclosure of a bis-triazolylbiaryl diol structure for silver halide color photographic film. However, actual compounds were neither disclosed nor exemplified.

With the exception of the isolated attempts summarized above to overcome the deficiencies of the existing stabilizers, the problems of high volatility and poor retention still remain largely unsolved.

It is therefore an object of this invention to provide novel benzotriazole UV absorbers which have the required low volatility without sacrificing compatibility and permanence. It will be apparent from the description below that the benzotriazoles of the present invention are efficient UV stabilizers, have very low volatility, good compatibility, and high permanence, providing protection at long wavelengths without yellowing.

SUMMARY OF THE INVENTION

The present invention is a composition of matter comprising a benzotriazole compound selected from the group consisting of a (2H-benzotriazol-2-yl)-biaryldiol compound, a bis-(2H-benzotriazol-2-yl)-biaryldiol compound, an N-oxide thereof, and a mixture thereof. We have discovered that (2H-benzotriazol-2-yl)-biaryldiols, bis-(-2H-benzotriazol-2-yl)-biaryldiols, and particularly a mixture thereof have the required low volatility without sacrificing compatibility with the polymer to which they are added, so that loss of the stabilizer either through volatilization during processing or through migration of the stabilizer to the surface of the polymer and eventual loss is minimized or prevented entirely.

This invention also provides a composition of matter comprising an azo compound selected from the group consisting of a (2-nitroarylazo)biaryldiol compound, a bis-(2-nitroarylazo)biaryldiol compound, and a mixture thereof.

This invention also provides a process for preparing a bis-benzotriazole compound, which comprises: oxidatively dimerizing a monomeric benzotriazole having an unsubstituted 4,6-position, a position para- or ortho- to the hydroxy group.

This invention also provides a process for preparing an azo compound, comprising: contacting a 2-nitroaryldiazonium salt and a biaryl diol at a temperature, pH, and length of time sufficient to produce an azo compound selected from the group consisting of (2-nitroarylazo)-biaryldiol, bis-(2-nitroarylazo)-biaryldiol, and a mixture thereof.

This invention is also a process for preparing a benzotriazole compound by reductive cyclization of an azo-compound, said process comprising: contacting a reducing agent and an azo compound selected from the group consisting of a (2-nitroarylazo)-biaryldiol, a bis-(2-nitroarylazo)-biaryldiol, and a mixture thereof, optionally in the presence of a catalyst, at a temperature and for a length of time sufficient to produce a benzotriazole selected from the group consisting of a (2H-benzotriazol-2-yl)-biaryldiol, a bis-(2H-benzotriazol-2-yl)-biaryldiol, an N-oxide thereof, and a mixture thereof.

This invention is also a degradation stable composition, comprising: (i) a degradable polymer; and (ii) a stabilizingly effective amount of a benzotriazole selected from the group consisting of a (2H-benzotriazol-2-yl)-biaryldiol compound, a bis-(2H-benzotriazol-2-yl)-biaryldiol compound, an N-oxide thereof, and a mixture thereof.

Finally, this invention is a method of stabilizing a degradable polymer, said method comprising: adding to said degradable polymer a stabilizingly effective amount of a benzotriazole selected from the group consisting of a (2H-benzotriazol-2-yl)-biaryldiol compound, a bis-(2H-benzotriazol-2-yl)-biaryldiol compound, an N-oxide thereof, and a mixture thereof.

The advantages of this invention include the following:

(1) The novel benzotriazoles of the invention are highly efficient light stabilizers;
(2) Due to their dimeric structure, the benzotriazoles of the present invention have very low volatility and therefore high permanence in the polymer;
(3) They absorb UV light at longer wavelengths than their non-dimeric or alkylene bridged dimeric counterparts. For example, the dimeric 3,3'-bis-(2H-benzotriazol-2-yl)-5,5'-di-tert-octyl-1,1'-biphenyl-2,2'-diol has an absorption maximum at longer wavelengths than either the monomeric 2-(2H-benzotriazol-2-yl)-4-tert-octyl-phenol known as CYASORB® UV-5411 Light Stabilizer or the methylene bridged 2,2'-methylenedi{6-(2-benzotriazolyl)-4-tert-octyl-phenol} known as MIXXIM BB/100® UV Absorber.
(4) They have good compatibility with polymers which commonly require stabilization;
(5) They are essentially colorless compounds and do not impart any yellowing to the stabilized polymers;
(6) Mixtures of the (2H-benzotriazol-2-yl)-biaryldiols and the bis-(2H-benzotriazol-2-yl)-biaryldiols absorb UV light over a broader range of wavelengths than the individual benzotriazoles. This provides protection against a broader spectrum of exposure conditions;
(7) (2H-benzotriazol-2-yl)-biaryldiols and the bis-(2H-benzotriazol-2-yl)-biaryldiols may also be useful as antioxidants due to phenolic moieties;
(8) 3,3'-Bis-(2H-benzotriazol-2-yl)-5,5'-di-methyl-1,1'-biphenyl-2,2'-diol and 3,3'-bis-(2H-benzotriazol-2-yl)-1,1'-biphenyl-2,2'-diol offer unexpectedly high synthetic yields; and
(9) 3,3'-bis-(2H-benzotriazol-2-yl)-1,1'-biphenyl-2,2'-diol provides an improved ability to stabilize polymers, particularly polycarbonates.

Polymeric materials that may be stabilized include: polyolefins, polyesters, polyethers, polyketones, polyamides, polyurethanes, polystyrenes, polyacrylates, polyacetals, polyacrylonitriles, polybutadienes, ABS, SAN (styrene acrylonitrile), ASA (acrylate styrene acrylonitrile), cellulosic acetate butyrate, cellulosic polymers, polyimides, polyamideimides, polyetherimides, polyphenylsulfide, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates,carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers of amines or blocked amines with activated unsaturated and/or methylene compounds, ketimines with activated unsaturated and methylene compounds, polyketimines in combination with unsaturated acrylic polyacetoacetate resins/polyketimines in combination with unsaturated acrylic resins, radiation curable compositions, epoxymelamine resins, organic dyes, cosmetic products, cellulose-based paper formulations, photographic film paper, ink, and blends thereof.

DETAILED DESCRIPTION OF THE INVENTION

Disclosed herein are novel benzotriazole UV light stabilizers and their precursors. Processes for making these compositions are also disclosed. The benzotriazole compounds of this invention are prepared by oxidative dimerization of a benzotriazole compound, or by reductive cyclization of the corresponding (2-nitroarylazo)biaryldiols. The precursor azo compounds are prepared by a process which includes coupling of a 2-nitroaryldiazonium salt with a diaryl diol.

Also disclosed is a stabilized composition containing the benzotriazole stabilizers of the invention and a method of using the benzotriazole stabilizers to stabilize photodegradable polymers.

The novel stabilizers of the present invention have lower volatility and therefore have more permanence particularly during polymer processing and coating bakes, provide broader UV protection particularly at longer wavelengths, and are colorless producing non-yellowing films and articles when incorporated into degradable polymers.

The various aspects of the present invention are described in greater detail below.

This invention includes a composition of matter comprising a benzotriazole compound selected from the group consisting of a (2H-benzotriazol-2-yl)-biaryldiol compound, a bis-(2H-benzotriazol-2-yl)-biaryldiol compound, an N-oxide thereof, and a mixture thereof. Thus, a mixture comprising at least two of any of the preceding triazole compounds is contemplated by the present invention.

The term (2H-benzotriazol-2-yl)-biaryldiol compound in the context of the present invention includes compositions represented by the formula:

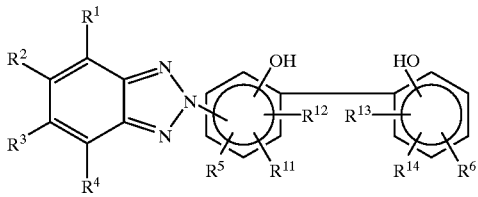

wherein $R^1$, $R^2$, $R^3$, $R^4$, $R^5$, $R^6$, $R^{11}$, $R^{12}$, $R^{13}$ and $R^{14}$ are the same or different and each is independently carboxy; cyano; halogen; or hydrogen; or linear, branched, or cyclic alkyl, alkenyl, aralkyl, acyl, alkoxy, alkoxyalkyl, alkoxycarbonyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted, with the proviso that one of the hydroxy groups is ortho- to a benzotriazole moiety. The substituents may be an amido; amino; azido; carboxylic acid; cyano; halogen e.g. fluoro, chloro, bromo, iodo; hydroxy; keto; nitro; sulfido; sulfonyl; sulfonic acid; sulfoxide; or thio group.

Preferably, $R^5$ and $R^6$ are —$CH_3$, —$C_2H_5$, n-$C_3H_7$, i-$C_3H_7$, n-$C_4H_9$, s-$C_4H_9$, t-$C_4H_9$, —$C_8H_{17}$, —$CH(C_2H_5)$ $C_5H_{11}$, t-$C_8H_{17}$, —$C_9H_{18}$, -Ph, —$C(CH_3)_2Ph$, —$C(CH_3)_2C_2H_5$, —$CH_2C(CH_3)_3$, —COOH, —C(O) $OC_8H_{17}$, —$C_3H_6OH$, —$C_2H_4COOH$, —$C_2H_4CONH_2$, —$C_2H_4COOCH_3$, —$C_2H_4COOCH_2CH_2OH$, —$CH_2CH_2OH$, —$C_2H_4COOCH_2CH_2OC(O)C(CH_3)CH_2$, —$C_2H_4COOC_8H_{17}$, —$C_2H_4COOCH(C_2H_5)C_5H_{11}$, —$C_2H_4COO(C_2H_4O)_8H$, —$C_2H_4COOCH_2CH(OH)$ $CH_2OC(O)C(CH_3)CH_2$ or —$C_2H_4COOCH(CH_2OH)$ $CH_2OC(O)C(CH_3)CH_2$. Preferably, $R^3$ is chloro, methoxy, thiophenoxy, phenyl sulfoxide, phenyl sulfone, —$SC_8H_{17}$, —$SC_{13}H_{27}$, —$S(O)C_{12}H_{25}$ or —$S(O)_2C_{12}H_{25}$.

The compositions represented by the term (2H-benzotriazol-2-yl)-biaryldiol compound are referred to herein as "mono" substituted benzotriazole compounds.

The benzotriazole of the invention may be selected from the group consisting of a 3-(2H-benzotriazol-2-yl)-1,1'-biaryl-2,2'-diol, a 3,3'-bis-(2H-benzotriazol-2-yl)-1,1'-biaryl-2,2'-diol, an N-oxide thereof, and a mixture of at least two of any of the preceding benzotriazoles.

The 3-(2H-benzotriazol-2-yl)-1,1'-biaryl-2,2'-diols may be represented by the formula:

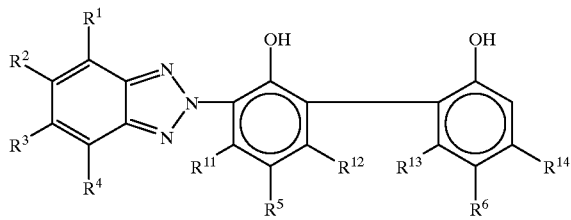

wherein $R^1$, $R^2$, $R^3$, $R^4$, $R^5$, $R^6$, $R^{11}$, $R^{12}$, $R^{13}$ and $R^{14}$ are as defined above.

The preferred halogens are chloro and bromo. The preferred compositions are those represented by the formula above wherein $R^5$ and $R^6$ are the same or different and each is independently selected from the group consisting of linear, branched, or cyclic alkyl of 1 to 16 carbon atoms and aralkyl of 7 to 18 carbon atoms, and wherein the remaining R groups are all hydrogen.

Particularly preferred are compositions represented by the formula above wherein $R^5$ and $R^6$ are the same and are selected from the group consisting of tert-octyl, tert-butyl, methyl, and cumyl; and wherein the remaining R groups are all hydrogen. The compounds symmetrically substituted on benzotriazole rings and the phenolic rings are noted herein as being synthetically more accessible than their non-symmetrical counterparts.

Examples of the particularly preferred compositions include the following classes of compounds described by the above formula:

(1) compounds wherein $R^5$ and $R^6$ are tert-octyl;

(2) compounds wherein $R^5$ and $R^6$ are methyl;

(3) compounds wherein $R^5$ and $R^6$ are hydrogen;

(4) compounds wherein $R^5$ and $R^6$ are tert-butyl; or (5) compounds wherein $R^5$ and $R^6$ are cumyl.

The term bis-(2H-benzotriazol-2-yl)-biaryldiol compound in the context of the present invention refers to compositions represented by the formula:

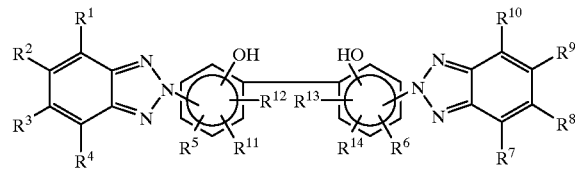

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are the same or different and each is independently carboxy; cyano; halogen; or hydrogen; or linear, branched, or cyclic alkyl, alkenyl, aralkyl, acyl, alkoxy, alkoxyalkyl, alkoxycarbonyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted, with the proviso that each hydroxy group is ortho- to a benzotriazole moiety.

Preferably, $R^5$ and $R^6$ are —H, —$CH_3$, —$C_2H_5$, n-$C_3H_7$, i-$C_3H_7$, n-$C_4H_9$, s-$C_4H_9$, t-$C_4H_9$, —$C_8H_{17}$, —$CH(C_2H_5)$ $C_5H_{11}$, t-$C_8H_{17}$, —$C_9H_{18}$, -Ph, —$C(CH_3)_2Ph$, —$C(CH_3)_2C_2H_5$, —$CH_2C(CH_3)_3$, —COOH, —C(O) $OC_8H_{17}$, —$C_2H_4COOH$, —$C_2H_4CONH_2$, —$C_2H_4COOCH_3$, —$C_2H_4COOCH_2CH_2OH$, —$CH_2CH_2OH$, —$C_2H_4COOCH_2CH_2OC(O)C(CH_3)CH_2$, —$C_2H_4COOC_8H_{17}$, —$C_2H_4COOCH(C_2H_5)C_5H_{11}$, —$C_2H_4COO(C_2H_4O)_8H$, —$C_2H_4COOCH_2CH(OH)$ $CH_2OC(O)C(CH_3)CH_2$ or —$C_2H_4COOCH(CH_2OH)$ $CH_2OC(O)C(CH_3)CH_2$. Preferably, $R^3$ and $R^8$ are hydrogen, chloro, methoxy, thiophenoxy, phenyl sulfoxide, phenyl sulfone, —$SC_8H_{17}$, —$SC_{13}H_{27}$, —$S(O)C_{12}H_{25}$ or —$S(O)_2C_{12}H_{25}$.

The compositions represented by the term bis-(2H-benzotriazol-2-yl)-biaryldiol compound are referred to herein as "bis" substituted benzotriazole compounds.

The 3,3'-bis-(2H-benzotriazol-2-yl)-1,1'-biaryl-2,2'-diols of the invention may be represented by the formula:

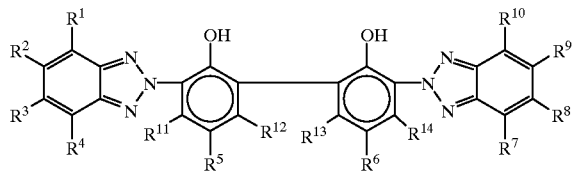

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above.

Also particularly preferred are compositions which comprise a mixture of the "mono" and "bis" substituted benzotriazole compounds.

The benzotriazole stabilizers of the present invention have many unexpected advantages over the stabilizers of the prior art. Some of these advantages are described below.

Surprisingly, mixtures of the (2H-benzotriazol-2-yl)-biaryldiols and the bis-(2H-benzotriazol-2-yl)-biaryldiols absorb UV light over a broader range of wavelengths than the individual benzotriazoles, providing protection against a broader spectrum of potentially damaging ultraviolet light. The preferred mixtures are those wherein the mole ratio of the 3,3'-bis-(2H-benzotriazol-2-yl)-1,1'-biaryl-2,2'-diol to the 3-(2H-benzotriazol-2-yl)-1,1'-biaryl-2,2'-diol is from about 99:1 to about 1:1.

The benzotriazoles of the present invention have very low volatility and therefore high permanence in the polymer. Below is a comparison of the volitily of benzotriazoles and bis-benzotriazoles.

| Compound | Description | TGA T-10%* (° C.) |
|---|---|---|
| Tinuvin ®-234 | Dicumyl Benzotriazole | 312 |
| LA-31 ® | Methylene Bis (UV-5411) | 380 |
| COMPOUND 1 | Bis Octyl | 381 |
| Unsubst. "monomer" | | 179 |
| COMPOUND 5 | Unsubst. dimer | 383 |
| COMPOUND 3 | Bis-Methyl | 377 |
| UV-5411 | Octyl Benzotriazole | 245 |
| Tinuvin P ™ | Methyl Benzotriazole | 205 |

THE RELATIVE VOLATILITY OF BENZOTRIAZOLES AND BIS-BENZOTRIAZOLES

*Temperature at which 10% wt. loss is observed during TGA analysis

They also have good compatibility with polymers which commonly require stabilization. Additionally, they are essentially colorless compounds, and unlike the sulfur containing benzotriazoles disclosed in PCT Publication No. 92/14717, they do not impart any yellowing to the stabilized polymers.

The higher solubility of 3,3'-bis-(2H-benzotriazol-2-yl)-5,5'-di-tert-octyl-1,1'-biphenyl-2,2'-diol in xylene (6.0 gram/100 ml) than the solubility of the methylene bridged 2,2'-methylene-di{6-(2-benzotriazolyl)-4-tert-octyl-phenol} known as MIXXIM BB/100® UV Absorber (2.5 gram/100 ml) is indicative of the superior compatibility of the benzotriazole stabilizers of the present invention over the stabilizers known in the art.

The high molar absorptivity of 3,3'-bis-(2H-benzotriazol-2-yl)-5,5'-di-tert-octyl-1,1'-biphenyl-2,2'-diol, $\epsilon_{310}$=25,600 (toluene) and $\epsilon_{353}$=28,300 (toluene) are indicative of high ultraviolet absorption efficiency of the benzotriazole stabilizers of the present invention.

A reliable indication of the volatility of benzotriazole stabilizers is the temperatures at which 10 wt % loss occurs ($TGA_{T=10\%}$). In a Thermal Gravimetric Analysis (TGA) experiment, the 3,3'-bis-(2H-benzotriazol-2-yl)-5,5'-di-tert-octyl-1,1'-biphenyl-2,2'-diol had its $TGA_{T=10\%}$ point at 384° C., a temperature much higher than that of the methylene bridged 2,2'-methylenedi{6-(2-benzotriazolyl)-4-tert-octyl-phenol} known as MIXXIM BB/100® UV Absorber ($TGA_{T=10\%}$=370° C.) and the monomeric 2-(2H-benzotriazol-2-yl)-4-tert-octyl-phenol known as CYASORB® UV-5411 Light Stabilizer ($TGA_{T=10\%}$=247° C.), indicative of the low volatility of the benzotriazole stabilizers of the present invention over the stabilizers previously known in the art.

The bis-benzotriazoles of the invention absorb UV light at longer wavelengths than their non-dimeric or alkylene bridged dimeric counterparts. For example, the dimeric 3,3'-bis-(2H-benzotriazol-2-yl)-5,5'-di-tert-octyl-1,1'-biphenyl-2,2'-diol of the present invention absorbs at $\lambda_{max}$ (toluene)=353 nm. In contrast, the monomeric 2-(2H-benzotriazol-2-yl)-4-tert-octyl-phenol absorbs at a much lower wavelength, at $\lambda_{max}$(toluene)=346 nm. Furthermore, the methylene bridged 2,2'-methylenedi{6-(2-benzotriazolyl)-4-tert-octyl-phenol} has an absorption at $\lambda_{max}$(toluene)=350 nm, also substantially shorter than that of the bis-benzotriazoles of the present invention.

It is apparent from the above that the benzotriazoles of the present invention are efficient UV stabilizers, are colorless, have very low volatility, good compatibility, and high permanence, providing protection at long wavelengths.

As mentioned above, the present invention includes a composition of matter comprising an azo compound selected from the group consisting of a (2-nitroarylazo)biaryl diol compound, a bis-(2-nitroarylazo)biaryl diol compound, and a mixture thereof.

The azo compound is typically selected from the group consisting of a 3-(2-nitroarylazo)-1,1'-biaryl-2,2'-diol, a 3,3'-bis-(2-nitroarylazo)-1,1'-biaryl-2,2'-diol, and a mixture thereof, although the 3-(2-nitroarylazo)-1,1'-biary-4,4'-diol and the corresponding 3,3'-bis-(2-nitroarylazo)-1,1'-biaryl-4,4'-diols are also usable.

The 3-(2-nitroarylazo)-1,1'-biaryl-2,2'-diol may be generically represented by the formula:

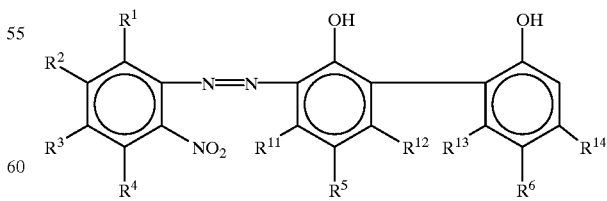

wherein $R^1$, $R^2$, $R^3$, $R^4$, $R^5$, $R^6$, $R^{11}$, $R^{12}$, $R^{13}$ and $R^{14}$ are as defined above.

The 3,3'-bis-(2-nitroarylazo)-1,1'-biaryl-2,2'-diols are represented by the formula:

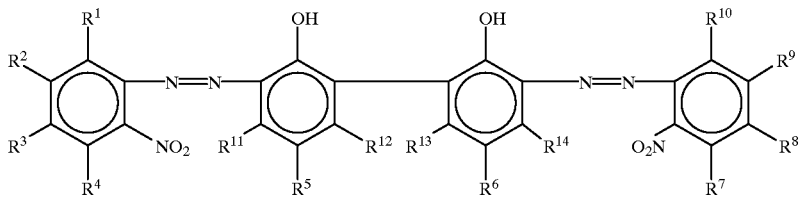

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above.

Also preferred are compositions which comprise a mixture of the "mono" and the "bis" substituted azo compounds because they can be used to prepare the preferred mixtures of the "mono" and "bis" substituted benzotriazole compounds. The preferred mixtures are those wherein the mole ratio of 3,3'-bis-(2-nitroarylazo)-1,1'-biaryl-2,2'-diol to 3-(2-nitroarylazo)-1,1'-biaryl-2,2'-diol is from about 99:1 to about 1:1.

The benzotriazole compounds of this invention may be prepared by: (1) oxidatively dimerizing a monomeric benzotriazole having an unsubstituted position para- or ortho- to the phenolic hydroxy; or (2) reductively cyclizing a mono- or bis-(2-nitroarylazo)biaryldiol.

In the direct approach of oxidative dimerization, the bis-benzotriazole compounds of this invention are prepared by oxidatively dimerizing a monomeric benzotriazole having an unsubstituted 4- or 6-position (i.e. para- or ortho- to the hydroxy group).

The process for preparing the bis-benzotriazole compound by oxidative dimerization comprises:

contacting an oxidizing reagent and a monomeric benzotriazole represented by the formula:

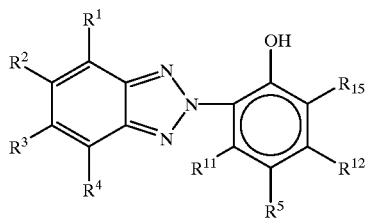

wherein $R^1$, $R^2$, $R^3$, $R^4$, $R^5$, $R^{11}$, $R^{12}$ and $R^{15}$ are as defined above, with the proviso that at least one of $R^5$ and $R^{15}$ is hydrogen; said contacting being carried out at a temperature and for a length of time sufficient to produce a bis-benzotriazole. In one embodiment the dimerization is carried out in the presence of about 0.1 to about 5% water.

Alternatively, a process for producing bis-benzotriazoles may comprise contacting an oxidizing agent and a compound of the above formula wherein $R^1$, $R^2$, $R^3$ and $R^4$ are defined as above and both $R^5$ and $R^{15}$ are hydrogen (synthesis of compounds of this type are described in Aust. J. Chem., Vol.38, 1163, 1985) to produce a bis-benzotriazole of the formula:

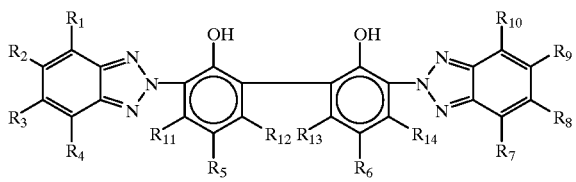

wherein $R^5$ and $R^6$ are hydrogen. Further reaction (e.g. alkylation, halogenation, or acylation), either in situ or in a separate step, may be carried out to produce benzotriazoles of the above formula wherein $R^5$ and $R^6$ are defined above.

Examples of the preferred benzotriazoles include 2-(2H-benzotriazol-2-yl)-4-tert-octyl-phenol available from CYTEC INDUSTRIES, West Paterson, N.J., under the tradename CYASORB® UV-5411 Light Stabilizer, 2-(2H-benzotriazol-2-yl)-4-methyl-phenol available from CIBA SPECIALTIES, Hawthorne, N.Y., under the tradename TINUVIN® P Light Stabilizer, 2-(2H-benzotriazol-2-yl)-4-tert-pentyl-phenol, 2-(2H-benzotriazol-2-yl)-4-tert-butyl-phenol, and 2-(2H-benzotriazol-2-yl)-4-cumyl-phenol. When not available commercially, the monomeric benzotriazoles usable in the oxidative dimerization process may be prepared by the general procedures disclosed in U.S. Pat. Nos. 3,773,751; 3,998,804; 4,275,004; 4,347,180; and 4,859,726.

The oxidizing reagents which are usable include an oxidizing reagent selected from the group consisting of oxygen, air, hydrogen peroxide, a persulfate salt such as sodium or potassium persulfate, a reagent comprising a metal selected from the group consisting of chromium, manganese, iron, cobalt, nickel, copper, cerium, lead, mercury, and silver, and a mixture of any of the preceding reagents. The preferred oxidizing reagents are compounds of iron. They include iron(III) halides such as iron(III) chloride and iron(III) bromide, ferricyanide salts such as potassium ferricyanide, other salts such as iron(III) nitrate and iron(III) sulfate and the like. Iron(II) salts in combination with an oxidizing agent capable of in situ generating iron(III) may also be used. Preferred solvents are water, alcohols, such as methanol, ethanol, isopropanol and tert-butanol, chlorinated solvents, such as methylene chloride, chloroform, ethylene dichloride, chlorobenzene, and polychlorobenzenes, ethers, such as diethyl ether, diphenyl ether, methyl tert-butyl ether, and tetrahydrofuran, aliphatic organic solvents, such as hexane, cyclohexane, and heptane, mixed aliphatic solvents such as naphtha, organic aromatic solvents such as toluene, xylene, and tetrahydronaphthalene, super critical fluids, such as super critical carbon dioxide, and mixtures of any of the above solvents.

Potassium ferricyanide in an aqueous alkaline solution has been found to be effective, particularly when using a two phase system of an aqueous alkaline layer with a substantially water immiscible organic layer such as a hydrocarbon, halocarbon, or ether layer. Ferric chloride in neutral or acidic solution has been also found to be effective. In one embodiment, about 4–20 mole percent of water is used with iron chloride and found to give improved yields. Heterogeneous conditions have been effective when using metal oxides such as manganese dioxide, lead dioxide, mercuric oxide, and silver(I) oxide. The use of metal oxides in polar and nonpolar solvents has been found to be satisfactory.

In the reductive cyclization approach, the mono- or bis-benzotriazole compounds of this invention are prepared by benzotriazole ring formation using a mono- or bis-(2-nitroarylazo)biaryldiol. The process comprises contacting a mono- or bis-(2-nitroarylazo)biaryldiol and a reducing agent at a temperature and length of time sufficient to produce a mono- or bis-benzotriazole compound. Of course, a mixture of mono- and bis-benzotriazoles is obtained when a mixture of mono- or bis-(2-nitroarylazo)biaryldiol is used as the reactant. The reduction may be carried out electrochemically or more commonly, chemically. In the case of chemical reduction, a chemical reducing agent is used. Suitable chemical reducing agents include hydrogen, a metal reducing agent, a sulfur compound, and a nitrogen compound. The preferred metal reducing agent is zinc. Typically, the reduction is carried out using hydrogen in the presence of a hydrogenation catalyst such as platinum or palladium compounds. The benzotriazole N-oxides are known intermediates in the reduction of nitroarylazo compounds, and may be present as an impurity in the final product. Alternately, the proportion of N-oxide can be maximized by modifying the reaction conditions (i.e. stoichiometry, temperature, reaction drive, etc.)

The starting materials from which the benzotriazole compounds of this invention are prepared are the mono- or bis-(2-nitroarylazo)biaryldiols, sometimes referred to herein as "azo compounds." The azo compounds are prepared by a process which includes coupling of a 2-nitroaryldiazonium salt with a biaryl diol. The various aspects of the process are described in greater detail below.

The azo compounds of the present invention are prepared from the coupling of a diazonium salt and a phenol compound. Diazonium salts are well known intermediates often used in the preparation of azo compounds by coupling with phenols, as disclosed in the previously mentioned U.S. Pat. Nos. 3,773,751; 3,998,804; 4,275,004; 4,347,180; and 4,859,726.

As phenolic starting materials, several 5,5'-disubstituted 2,2'-dihydroxy biphenyls are available from Enzymol International, Inc., Columbus, Ohio. Others may be prepared by known chemical, enzymatic, and photochemical methods. For example, 5,5'-di-tert-butyl-2,2'-dihydroxybiphenyl may be prepared by oxidatively dimerizing 2,4-di-tert-butyl phenol according to a method described in Ann., Vol. 645, page 25(1961) and thereafter debutylating the tert-butyl group ortho- to the hydroxy group according to a procedure described in Org. Prep. Proced. Int., Vol. 6, No. 3, page 117(1974). Other 2,2'-dihydroxy biphenyls may be prepared by known procedures such as those described in the following patents and publications: Jap. Pat. No. 62-077341, British Pat. 1,508,368, and U.S. Pat. Nos. 4,380,676 and 3,247,262; J. Indian Chem. Soc., Vol. 61, No. 2, page 142(1984), Tetrahedron, Vol. 48, No. 43, page 9483(1992), J. Biol. Chem., Vol. 145, page 463(1942), and J. Indian Chem. Soc., Vol. 67, No. 5, page 387(1990).

As indicated above, the present invention is also a process for preparing an azo compound, comprising: contacting a 2-nitroaryldiazonium salt and a biaryl diol at a temperature, pH, and length of time sufficient to produce an azo compound selected from the group consisting of (2-nitroarylazo)-biaryldiol compound, a bis-(2-nitroarylazo)-biaryldiol compound, and a mixture thereof.

The preferred 2-nitroaryldiazonium salt is 2-nitrophenyldiazonium bisulfate and the biaryl diol is 5,5'-di-tert-octyl-1,1'-biphenyl-2,2'-diol. The preferred azo products are those selected from the group consisting of 3-(2-nitrophenylazo)-5,5'-di-tert-octyl-1,1'-biphenyl-2,2'-diol and 3,3'-bis-(2-nitrophenylazo)-5,5'-di-tert-octyl-1,1'-biphenyl-2,2'-diol.

Reductive cyclization of 2-nitroarylazo compounds to the corresponding benzotriazole compounds is a well known transformation and has been previously used to prepare 2-(2-hydroxyaryl)benzotriazole compounds useful as UV absorbers. For example, previously mentioned U.S. Pat. Nos. 3,773,751 and 4,859,726 disclose reductive cyclization of 2-nitroarylazo compounds to the corresponding benzotriazole compounds using metal reducing agents and U.S. Pat. Nos. 3,978,074; 4,141,903; 4,219,480; 4,230,867; and 5,187,289; and Canadian Pat. No. 1,155,856 disclose reductive cyclization using hydrogen in the presence of a reduction catalyst.

We now disclose a process for preparing a benzotriazole, comprising: contacting a reducing agent and an azo compound selected from the group consisting of a (2-nitroarylazo)-biaryldiol compound, a bis-(2-nitroarylazo)-biaryldiol compound, and a mixture thereof, optionally in the presence of a catalyst, at a temperature and for a length of time sufficient to produce a compound selected from the group consisting of a (2H-benzotriazol-2-yl)-biaryldiol compound, a bis-(2H-benzotriazol-2-yl)-biaryldiol compound, an N-oxide thereof, and a mixture thereof.

The preferred azo compound usable in process of the invention is an azo compound selected from the group consisting of 3-(2-nitrophenylazo)-5,5'-di-tert-octyl-1,1'-biphenyl-2,2'-diol, 3,3'-bis-(2-nitrophenylazo)-5,5'-di-tert-octyl-1,1'-biphenyl-2,2'-diol, and a mixture thereof. The preferred reducing agent is zinc or hydrogen. When hydrogen is the reducing agent, the reduction is carried out in the presence of a hydrogenation catalyst which, typically, is a Group VII metal. Particularly preferred are catalysts which comprise a metal supported on carbon. The metal is preferably selected from the group consisting of platinum and palladium.

In the practice of the invention, the reductive cyclization is carried out at a reduction temperature in the range of from about 20° C. to about 90° C. and preferably at a temperature in the range of from about 40° C. to about 80° C.

The two processes described above may be integrated into a single process for preparing a triazole compound, comprising: (a) contacting a 2-nitroaryldiazonium salt and a biaryldiol at a temperature, pH, and length of time sufficient to produce an azo compound selected from the group consisting of (2-nitroarylazo)-biaryldiol compound, a bis-(2-nitroarylazo)-biaryldiol compound, and a mixture thereof; and thereafter (b) contacting a reducing agent and the azo compound of step (a), optionally in the presence of a catalyst, at a temperature and for a length of time sufficient to produce a compound selected from the group consisting of a (2H-benzotriazol-2-yl)-biaryldiol compound, a bis-(2H-benzotriazol-2-yl)-biaryldiol compound, an N-oxide thereof, and a mixture thereof.

The preferred embodiments of the integrated process comprise those described hereinabove. For example, the preferred 2-nitroaryldiazonium salt is 2-nitrophenyldiazonium bisulfate and the biaryl diol is 5,5'-di-tertiaryoctyl-1,1'-biphenyl-2,2'-diol. The preferred azo compound usable in step (b) of the process is the azo product of step (a), which is an azo compound selected from the group consisting of 3-(2-nitrophenylazo)-5,5'-di-tert-octyl-1,1'-biphenyl-2,2'-diol, 3,3'-bis-(2-nitrophenylazo)-5,5'-di-tert-octyl-1,1'-biphenyl-2,2'-diol, and a mixture thereof. The preferred reducing agent is zinc or hydrogen. In reductions using hydrogen, the hydrogenation is carried out in the presence of a hydrogenation catalyst which, typically, is a Group VII metal. Particularly preferred are catalysts which comprise a metal supported on carbon. The metal is preferably selected from the group consisting of platinum and palladium. In the practice of the invention, the reductive cyclization step is carried out at a reduction temperature in the range of from about 20° C. to about 90° C. and preferably at a temperature in the range of from about 40° C. to about 80° C.

The present invention is also a degradation stable composition, which comprises: (i) a degradable polymer; and (ii) a stabilizingly effective amount of a benzotriazole selected from the group consisting of a (2H-benzotriazol-2-yl)-biaryldiol compound, a bis-(2H-benzotriazol-2-yl)-biaryldiol compound, an N-oxide thereof, and a mixture thereof. The composition may further comprise a (2-H benzotriazol-2-yl)-phenol compound.

More specifically, the degradation stable composition of the invention may contain a benzotriazole selected from the group consisting of a 3-(2-H-benzotriazol-2-yl)-1,1-biaryl-2,2'-diol, a 3,3'-bis-(2H-benzotriazol-2-yl)-1,1'-biaryl-2,2'-diol, an N-oxide thereof and a mixture thereof.

The preferred benzotriazole UV stabilizer is selected from the group consisting of a 3-(2H-benzotriazol-2-yl)-5,5'-di-alkyl-1,1'-biphenyl-2,2'-diol, a 3,3'-bis-(2H-benzotriazol-2-yl)-5,5'-di-alkyl-1,1'-biphenyl-2,2'-diol, a 3,3-bis-(2H-benzotriazol-2-yl)-1,1'-biphenyl-2,2'-diol, an N-oxide thereof, and a mixture thereof and is present in the degradable polymer at a stabilizingly effective level. Typically, the concentration of the benzotriazole is in the range of from about 0.01 weight percent to about 5.0 weight percent.

The degradation stable compositions of the present invention may comprise one or more stabilizers or additives from different classes of compounds. Each stabilizer or additive, or a combination thereof is incorporated into the degradable polymer to serve a specific function well known in the art.

The present invention is also a method of stabilizing a degradable polymer, said method comprising: adding to said degradable polymer a stabilizingly effective amount of a benzotriazole selected from the group consisting of a (2H-benzotriazol-2-yl)-biaryldiol compound, a bis-(2H-benzotriazol-2-yl)-biaryldiol compound, an N-oxide thereof, and a mixture thereof.

More specifically, a benzotriazole selected from the group consisting of a 3-(2-H-benzotriazol-2-yl)-1,1-biaryl-2,2'-diol, a 3,3'-bis-(2H-benzotriazol-2-yl)-1,1'-biaryl-2,2'-diol, an N-oxide thereof and a mixture thereof may be advantageously added to the degradable polymer.

Other additives such as those described above may also be used to give the degradable polymer the desired properties for a particular end use.

Uses of the Benzotriazoles

As indicated earlier, the novel benzotriazoles of the present invention are particularly useful as ultraviolet light absorber additives for stabilizing a wide variety of organic materials including, for example, various organic polymers (both cross-linked and thermoplastic), photographic materials and dye solutions for textile materials, as well as in ultraviolet light screening agents (such as sunscreen). The novel benzotriazoles of the present invention can be incorporated into such material in any one of a variety of conventional manners, including for example, chemical bonding to the material (typically to a polymer), as a component in a light stabilizing composition such as a coating or solution, or as a component in a UV screening composition such as a sunscreen composition.

In one embodiment of the present invention, the benzotriazoles of the present invention can be employed to stabilize materials which are subject to degradation by ultraviolet radiation by incorporating the presently claimed compounds into such materials, especially organic polymers.

The degradable polymer may be any polymer requiring stabilization and includes homopolymers and copolymers of various monomers. It may be an addition polymer, a condensation polymer, a graft polymer, a thermosetting polymer, a photopolymer, a polymer blend or a thermoplastic polymer. It may be in the form of a fiber, a polymer film such as polypropylene films, a thin film such as solvent based coatings, water based coatings, stoving lacquers, powder coatings, gel coats and the like, or it may be in the form of molded articles. Examples of degradable polymers which can be stabilized include, but are not limited to:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene, and cycloolefins such as cyclopentene and norbornene; for example, polyethylenes (which optionally can be cross-linked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE) or polypropylene (PP) or polymers of ethylene propylene diene monomer (EPDM).
2. Copolymers of one or more monoolefins and/or diolefins with carbon monoxide and/or with other vinyl monomers, including acrylic and methacrylic acid, acrylates and methacrylates, acrylamides, acrylonitriles, styrenes, vinyl acetate (such as ethylene/vinyl acetate copolymers (EVA)), vinyl halides, vinylidene halides, maleic anhydride, and allyl monomers such as allyl alcohol, allyl amine, allyl glycidyl ether and compounds thereof.
3. Hydrocarbon resins (such as $C_5$–$C_9$) including hydrogenated modifications thereof, and mixtures of polyalkylenes and starch.
4. Homo- and copolymers of styrenes such as styrene, p-methylstyrene and α-methylstyrene such as polystyrene, polyalphamethylstyrene, high impact polystyrene (HIPS).
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine, allyl glycidyl ether and compounds thereof.
6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; acrylonitrile/styrene/acrylonitrile polymers (ASA) styrene and acrylonitrile on ethylene/propylene/diene copolymers; styrene and acrylonitrile on polyalkyl acrylates or methacrylates; and styrene and acrylonitrile on acrylate/butadiene (ABS) copolymers.

7. Halogen-containing polymers such as poly vinyl chloride (PVC), chlorinated polyethylene (CPE), or polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride, other vinyl monomers or other polyvinyl halides.

8. Homo- and copolymers derived from α,β-unsaturated acids and compounds thereof such as acrylic acid, methacrylic acid, acrylates, methacrylates, acrylamides and acrylonitriles.

9. Copolymers of the monomers mentioned in (5) above with other unsaturated monomers such as olefins and diolefins (e.g., butadiene), styrenes, vinyl halides, maleic anhydride and allyl monomer such as allyl alcohol, allyl amine, allyl glycidyl ether and compounds thereof.

10. Homo- and copolymers derived from unsaturated alcohols and amines or the acyl compounds or acetals thereof, such as vinyl alcohol (including polyvinyl alcohol cross-linked polyvinyl alcohol), vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenic unsaturated monomers mentioned above.

11. Homo- and copolymers of cyclic ethers such as alkylene glycols and alkylene oxides, as well as copolymers with bisglycidyl ethers.

12. Polyacetals such as polyoxymethylene (POM) and those polyoxymethylenes which contain ethylene oxide as a comonomer; and polyoxymethylenes modified with thermoplastic polyurethanes, acrylates and/or MBS.

13. Polyphenylene oxides (PPO) and sulfides.

14. Polyurethanes (PUR) derived from hydroxy-functional components such as polyhydric alcohols, polyethers, polyesters, polyacrylics and/or polybutadienes on the one hand, and aliphatic and/or aromatic isocyanates on the other, as well as precursors thereof including isocyanate cross-linked polymers.

15. Polyamides (PA) and copolyamides derived from diamines, dicarboxylic acids and/or aminocarboxylic acids or the corresponding lactams, such as NYLON® plastics, e.g., polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyepoxides, polyethylene glycol, polypropylene glycol or polytetramethylene glycol; and polyamides condensed during processing (RIM polyamide systems).

16. Polyureas, polyimides, polyamide-imides, polyetherimides, polyesterimides, polyhydantoins and polybenzimidazoles.

17. Polyesters derived from dicarboxylic acids, diols and/or hydroxycarboxylic acids or the corresponding lactones, such as polyethylene terephthalate (PET), polybutylene terephthalate (PBT), polyethylene terephthalate, glycol modified (PETG), polyethylene terephthalate modified with 1,4-cyclohexanedimethanol (PCTG), poly-1,4-dimethylcyclohexane terepthalate and polyhydroxybenzoates, as well as block copolyether esters derived from hydroxyl-terminated ethers; and also polyesters modified with polycarbonate or MBS; PEN, PTT.

18. Polycarbonates (PC) and polyester carbonates such as resins are polycarbonates based on dihydric phenols such as 2,2-bis-(4-hydroxyphenyl)propane (bisphenol A); 2,4-bis (4-hydroxyphenyl)-2-methylbutane; 1,1-bis-(4-hydroxyphenyl)-cyclohexane; 2,2-bis-(3-chloro-4-hydroxyphenyl)propane; 4,4'-sulfonyldiphenol; and 1,1-bis-(4-hydroxyphenyl)-3,3,5-trimethylcyclohexane. Also preferred are polycarbonate copolymers incorporating two or more phenols, branched polycarbonates wherein a polyfunctional aromatic compounds is reacted with the dihydric phenol(s) and carbonate precursor, and polymer blends of which polycarbonate comprises a significant portion of the blend. Preferred resins for both layers are polycarbonates based on bisphenol A.

U.S. Pat. No. 5,288,788 also describes polycarbonates and polyester carbonates, especially aromatic polycarbonates, for example those based on 2,2-bis(4-hydroxyphenyl)propane or 1,1-bis(4-hydroxyphenyl)cyclohexane. Mixtures (polyblends) of such polymers with one another or with other polymers, for example with polyolefins, polyacrylates, polydienes or other elastomers in the form of impact strength modifiers.

Among those compounds, preference is given to the polycarbonates, polyesters, polyamides, polyacetals, polyphenylene oxides and polyphenylene sulfides, but especially to the polycarbonates. Those compounds are to be understood as being especially those polymers the constitutional repeating unit of which corresponds to the formula:

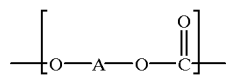

wherein A is a divalent phenolic radical. Examples of A are given inter alia in U.S. Pat. No. 4,960,863 and DE-A-3 922,496. A can be derived, for example, from hydroquinone, resorcinol, dihydroxybiphenylene or bisphenols in the broadest sense of the term, such as bis(hydroxyphenyl) alkanes, cycloalkanes, sulfides, ethers, ketones, sulfones, sulfoxides, α,α'-bis(hydroxyphenyl)-diisopropylbenzenes, for example the compounds 2,2-bis(4-hydroxyphenyl) propane, 2,2-bis(3,5-dimethyl-4-hydroxyphenyl)-propane, 2,2-bis(3,5-dichloro-4-hydroxyphenyl)propane, 1,1-bis(4-hydroxypehnyl)cyclohexane, or from the compounds of the formulae:

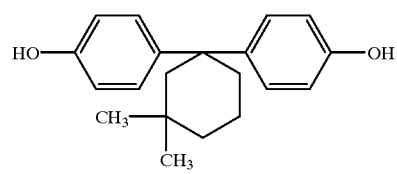

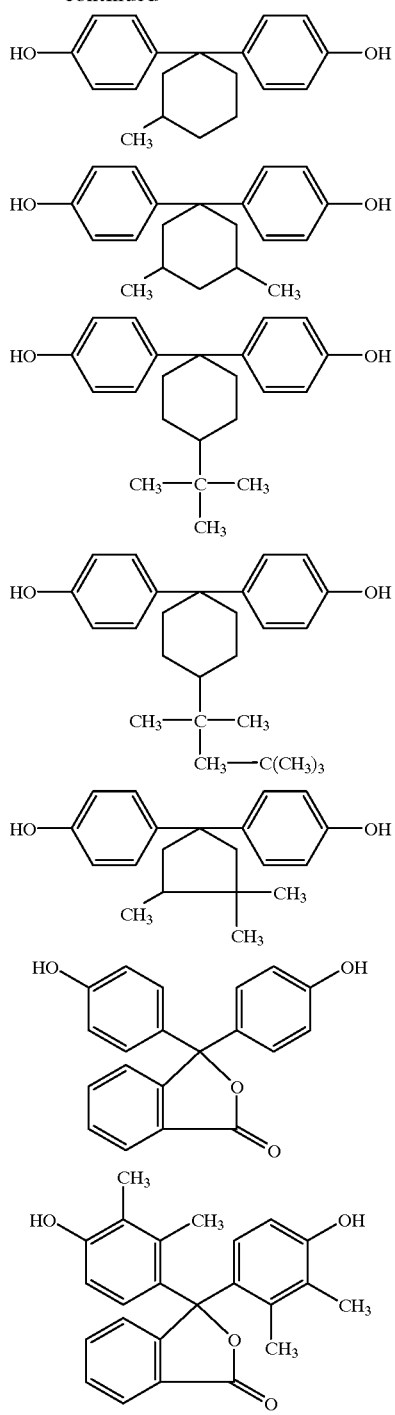

19. Polysulfones, polyether sulfones and polyether ketones.
20. Cross-linked polymers derived from aldehydes condensation resins such as phenol/formaldehyde resins, urea/formaldehyde resins and melamine/formaldehyde resins.
21. Drying and non-drying alkyd resins.
22. Unsaturated polyester resins derived from copolyesters of saturated and unsaturated dicarboxylic acids with polyhydric alcohols and vinyl compounds as crosslinking agents, and also halogen-containing modifications thereof.
23. Cross-linkable acrylic resins derived from substituted acrylates such as epoxy acrylates, hydroxy acrylates, isocyanato acrylates, urethane acrylates or polyester acrylates.
24. Alkyd resins, polyester resins and acrylate resins cross-linked with melamine resins, urea resins, isocyanates, isocyanurates, carbamates or epoxy resins.
25. Cross-linked epoxy resins derived from aliphatic, cycloaliphatic, heterocyclic and/or aromatic glycidyl compounds such as bisphenol A and bisphenol F, which are cross-linked with customary hardeners such as anhydrides or amines.
26. Natural polymers such as cellulose, rubber, gelatin and chemically modified homologous compounds thereof, including cellulose acetates, cellulose propionates and cellulose butyrates, nitrocellulose, or the cellulose ethers such as methyl cellulose, as well as rosins and their compounds.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
31. Aqueous emulsions of natural or synthetic rubber such as natural latex or latexes of carboxylated styrene/butadiene copolymers.
32. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
33. Radiation curable compositions containing ethylenically unsaturated monomers or oligomers and a polyunsaturated aliphatic oligomer.
34. Epoxymelamine resins such as light-stable epoxy resins cross-linked by an epoxy functional coetherified high solids melamine resin. The aminoresin-cross-linked polymer may be an aminoresin-cross-linked thermoset acrylic or an aminoresin-cross-linked thermoset polyester. The suitable aminoresins include alkylated and unalkylated melamine-formaldehyde resins, guanamine-formaldehyde resins, urea-formaldehyde resins, glycoluril formaldehyde resins and the like.
35. Organic dyes such as azo dyes (diazo, triazo, and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles, and perylene tetracarboxylic diimides.
36. Cosmetic products, such as skin lotions, collagen creams, sunscreen, facial make-up, etc., comprising synthetic materials such as antioxidants, preservatives, lipids, solvents surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.

37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.

38. Photographic film paper.

39. Ink.

As mentioned above, one particular advantage of the benzotriazoles of the present invention is with suitable functionality they can be chemically bound to such polymers, thereby greatly reducing the migration of such UV absorbers. The bonding mechanism of the of the presently claimed benzotriazoles involves the formation of a carbon-carbon, carbon-oxygen, or nitrogen-carbon bond between functionality on the benzotriazole and the "host" polymer. Such functionality can be in the form of, for example, vinylic, acetylenic, hydroxyl, amino, amido, or carbamoyl groups.

Incorporation of the benzotriazoles of the present invention can be brought about by copolymerization, copolyaddition, copolycondensation, by reaction with a polymer which carries suitable functional groups or by grafting as disclosed by CA 2,032,669 A1.

Bonding of the benzotriazoles of the invention can occur by polymerization or co-polymerization. Polymerization or copolymerization can be initiated by initiators, such as free radical, anionic and cationic types, or by actinic radiation, such as UV, electron beam, x-rays and gamma irradiation from a $Co^{60}$ source, as is well known to those in the polymerization art. Polymerization or copolymerization can be carried out in solution, in an emulsion, in a dispersion, in the melt, or in the solid state as is well known to those in the polymerization art.

In addition, bonding of the presently claimed benzotriazole compounds of the present invention can be brought about by copolyaddition or copolycondensation. Such incorporation is made by addition during the synthesis of an addition polymer or copolymer or by condensation during the synthesis of a condensation polymer or copolymer by methods known to those skilled in the art. For example, benzotriazoles containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

Alternately, the benzotriazoles of the invention may also be bonded to polymers by reaction with an oligomer and/or polymer which carries suitable functional groups. For example, at least one benzotriazole compound of the present invention can be added, optionally to unsaturated polyester resins, unsaturated polybutadiene oligomers or unsaturated rubbers and then cured by actinic radiation or by a free radical catalyst. Or, at least one benzotriazole compound of the present invention may be reacted with a polymer and/or oligomer such as polyesters, polyurethanes and polydiols with reactive end-groups, partially hydrolyzed polyvinylacetate, epoxy resins, polysiloxanes and polymers comprising maleic anhydride, either in the main chain or as a side-chain, by methods well known to those in the art.

Grafting is yet another way of bonding of the presently claimed benzotriazole compounds to polymers and/or oligomers. Grafting may be carried out in solution, in the melt, or in the solid state with the initiators or actinic radiation types discussed above for polymerization. Such benzotriazoles of the present invention may be grafted to saturated polymers, e.g., polyolefins and their copolymers such as polyethylene, polypropylene and poly(ethylene-vinyl acetate), or to polymers comprising unsaturated moieties, e.g., polybutadiene, polyisoprene, ethylene-propylene-(diene monomer) terpolymers and polystyrene and its copolymers.

The benzotriazoles of the present invention may be used in a wide variety of amounts in such applications depending upon such things as the material to be stabilized and the particular application. However, when employed as a stabilizing additive for materials such as organic polymers, the presently claimed benzotriazoles of the present invention are typically employed in amounts from about 0.01 to about 20 weight percent, preferably from about 0.01 to about 10 weight percent, and most preferably from about 0.02 to about 5 weight percent, based on the weight of the material to be stabilized. In screening applications such as sunscreening compositions, the benzotriazoles are utilized in the same relative amounts but based on the total weight of the screening agent.

In particular, the novel stabilizers can preferably be employed in compositions which contain a synthetic organic polymer, especially a thermoplastic polymer. Examples of preferred thermoplastic polymers are polyolefins and polymers comprising heteroatoms in the main chain. Also preferred are thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the organic polymers, for example into the synthetic organic and, in particular, thermoplastic polymers, can be carried out by addition of the novel benzotriazole compound and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices. An additional method of incorporating the novel mixtures into polymers comprises adding them before or during polymerization of the corresponding monomers or before crosslinking.

The novel mixtures can also be added to the polymers to be stabilized in the form of a master batch which comprises these compounds, for example, in a concentration of from about 2.5 to about 25 percent, preferably 5 to about 20 percent by weight of the polymer.

The novel mixtures can expediently be incorporated into the polymeric material by any number of methods, including those conventionally employed in the art, including by, for example: (a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion or injection molding. Therefore, the present invention additionally relates to the use of the polymer composition according to the invention for the production of a shaped article.

Depending upon their ultimate end use, the benzotriazoles of the present invention may be combined with a variety of additives conventionally employed in the UV stabilizing art. Examples of such additives include but are not limited to:

a. Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-($\alpha$-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylundec-1-yl)phenol; 2,4-dimethyl-6-(1-methylheptadec-1-yl)phenol; 2,4-dimethyl-6-(1-methyltridec-1-yl)phenol; CYANOX® 1790; CYANOX® 2246; and CYANOX® 425 Antioxidants, products of CYTEC INDUSTRIES, West Paterson, N.J.; IRGANOX® 1010 Antioxidant and IRGANOX® 1076 Antioxidant, products of CIBA SPECIALTIES, Hawthorne, N.Y.; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl -4-nonylphenol.

(iii) Hydroquinones and alkylated hydroquinones such as 2,6-di-tert-butyl-4-methoxyhenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.

(iv) Tocopherols such as $\alpha$-tocopherol (vitamin E), $\beta$-tocopherol, $\gamma$-tocopherol, $\delta$-tocopherol and mixtures thereof.

(v) Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.

(vi) Alkylidenebisphenols such as 2,2'-methylenebis(6-tert-butyl-4-methylphenol); 2,2'-methylenebis(6-tert-butyl-4-ethylphenol); 2,2'-methylenebis[4-methyl-6-($\alpha$-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-($\alpha$-methylbenzyl)-4-nonylphenol]; 2,2'-methylenebis[6-($\alpha$,$\alpha$-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O-, N- and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of $\beta$-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, and 4-hydroxymethyl-1-phospha-2,6,7-trioxabicyclo[2.2.2]octane.

(xiv) Esters of β-(5-tert-butyl-4-hydroxy-3-methylphenyl)propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, and 4-hydroxymethyl-1-phospha-2,6,7-trioxabicyclo[2.2.2]octane.

(xv) Esters of β-(3,5-dicyclohexyl-4-hydroxyphenyl)propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane, and 4-hydroxymethyl-1-phospha-2,6,7-trioxabicyclo[2.2.2]octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; N-allyldiphenylamine; 4-isopropoxydiphenylamine; N-phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl) amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl) amino]ethane; 1,2-bis(phenylamino)propane; (o-tolyl) biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono- and dialkylated tert-butyldiphenylamines; 2,3-dihydro-3,3-dimethyl-4H-1,4-benzothiazine; phenothiazine; a mixture of mono- and dialkylated tert-butyl/tert-octyl phenothiazines; a mixture of mono- and dialkylated tert-octylphenothiazines; N-allylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-ol.

b. UV-absorbers and light stabilizers (i) 2-(2'-Hydroxyaryl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole or 2-(2H-benzotriazol-2-yl)-4-tert-octyl-phenol known as CYASORB® UV-5411 Light Stabilizer, a product of CYTEC INDUSTRIES, West Paterson, N.J.; 2-(3',5'-di-tert-butyl-2'-hydroxyphenyl)-5-chlorobenzotriazole; 2-(3'-tert-butyl-2'-hydroxy-5'-methylphenyl)-5-chlorobenzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4-(1,1,3,3-tetramethylbutyl)-6-benzotriazole-2-yl phenol]; the transesterification product of 2-[3'-tert-butyl-5'-(2-methoxycarbonylethyl)-2'-hydroxyphenyl] benzotriazole with polyethylene glycol 300; [R—CH$_2$CH—COO(CH$_2$)$_3$]$_2$—where R=3'-tert-butyl-4'-hydroxy-5'-2H-benzotriazol-2-yl phenyl; and TINUVIN® 900 Light Stabilizer, a product of CIBA SPECIALTIES, Hawthorne, N.Y.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy compounds; and CYASORB® UV-531 Light Stabilizer, a product of CYTEC INDUSTRIES, West Paterson, N.J.

(iii) Esters of substituted and unsubstituted benzoic acids or salicylic acid compounds such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl-3,5-di-tert-butyl-4-hydroxybenzoate.

(iv) Acrylates or alkoxycinnamates such as ethyl α-cyano-β,β-diphenylacrylate; isooctyl α-cyano-β,β-diphenylacrylate; methyl α-carbomethoxycinnamate; methyl α-cyano-β-methyl-p-methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline.

(v) Nickel compounds including nickel (II) complexes of amines and thio-bis-phenols such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; and nickel complexes of 1-phenyl-4-lauroyl-5-hydroxypyrazole, with or without additional ligands.

(vi) Sterically hindered amines as well as the N compounds thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl) succinate; bis(1,2,2,6,6-pentamethylpiperidin-4-yl) sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(1-ethanoyl-2,2,6,6-tetramethylpiperidin-4-yl)pyrrolidin-2,5-dione; 3-dodecyl-1-(2,2,6,6-tetramethylpiperidin-4-yl) pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); N-(2,2,6,6-tetramethyl piperidine-4-yl)-n-dodecylsuccinimide; N-(1,2,2,6,6-pentamethylpiperidin-4-yl)-n-dodecylsuccinimide; 2-undecyl-7,7,9,9-tetramethyl-1-oxa-3,8-diaza-4-oxospiro[4.5]decane; oxo-piperanzinyl-triazines or so called PIP-T HALS, e.g., GOODRITE® 3034, 3150 and 3159 (BF Goodrich Chemical Co. Akron, Ohio) and similar materials disclosed in U.S. Pat. No. 5,071,981; photobondable HALS such as SANDUVOR® PR-31 AND PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. Examples of the tetramethylpiperidine derived HALS include CYASORB® UV-3346 Light Stabilizer, a product of CYTEC INDUSTRIES, West Paterson, N.J., SANDUVOR® 3055 HALS, SANDUVOR® 3056 HALS, and SANDUVOR® 3058 HALS, products of SANDOZ Corporation, Charlotte, N.C., CHIMASORB® 944 Stabilizer, a product of CIBA SPECIALTIES, Hawthorne, N.Y., TINUVIN® 622 Stabilizer and TINUVIN® 144 Stabilizer, both products of CIBA SPECIALTIES, Hawthorne, N.Y. See also generally U.S. Pat. Nos. 5,106,891, 4,740,542, 4,619,956, 4,426,471, 4,426,472, 4,356,307, 4,344,876, 4,314,933; GB-A-2269819, EP-A-309400, EP-A-309401, EP-A-309402 and EP-A-0434608, which are incorporated herein by reference in their entirety.

(vii) Oxamides, oxanilides, benzoxazinones or benzoxazoles such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines, such as 2,4,6-tris(2-hydroxy-4-octyloxyphenyl)-1,3,5-triazine; 2-(2-hydroxy-4-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2- hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine; and CYASORB® UV-1164L Light Stabilizer, a product of CYTEC INDUSTRIES, West Paterson, N.J.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

(d) Phosphites and phosphonites including peroxide decomposers such as alkyl phosphites, aryl phosphites, and aralkyl phosphites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite ULTRANOX® 618 Antioxidant; bis-(2,4-di-tert-butylphenyl) pentaerythritoldiphosphite ULTRANOX® 626 Antioxidant, both products of GE Specialty Chemicals, Parkersburg, W.V.; tris(2,4-di-tert-butylphenyl)phosphite; diisodecyl pentaerythritol diphosphite; bis(2,6-di-tert-butyl-4-methylphenyl)pentaerythritol diphosphite; bis(isodecyloxy) pentaerythritol diphosphite; bis(2,4-di-tert-butyl-6-methylphenyl)pentaerythritol diphosphite; bis(2,4,6-tris(tert-butyl)phenyl)pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl) methylphosphite; and bis(2,4-di-tert-butyl-6-methylphenyl) ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea compounds; hydrazine compounds; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide), and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers ("ionomers").

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Benzofuranones and indolinones such as those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyl] benzofuran-2-one; 3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; and 3-(3,5-dimethyl-4-pivaloyloxyphenyl)-5,7-di-tert-butyl-benzofuran-2-one.

(n) Sulfur containing antioxidants such as organic sulfides and disulfides and include distearyl thiodipropionate CYANOX® STDP Antioxidant, a product of CYTEC INDUSTRIES, West Paterson, N.J. and pentaerythritol tetrakis(beta-laurylthiopropionate) SEENOX® 412 S Antioxidant, a product of Witco Chemical Corporation, Brooklyn, N.Y. A person skilled in the art will know, for example, that one or more of these additives may be combined such as in CYANOX® 2777 Antioxidant, a product of CYTEC INDUSTRIES, West Paterson, N.J., which combines a phenolic antioxidant and a phosphite antioxidant. The composition may contain quenchers such as CYASORB® UV-1084 Light Stabilizer, a product of CYTEC INDUSTRIES, West Paterson, N.J., CYASORB® UV-531 Light Stabilizer, also a product of CYTEC INDUSTRIES, West Paterson, N.J.

(o) Other additives such as acid scavengers, antistatic agents, blowing agents, catalysts, clarifying agents, emulsifiers, fillers, flameproofing agents, fluorescent whitening agents, infrared absorbers, levelling assistants, lubricants, metal deactivators, mold release agents, nucleating agents, optical brighteners, pigments, plasticizers, and rheological additives.

The novel benzotriazoles of the present invention can also be employed in multilayer systems. In such systems, a polymer composition having 0.1 to about 20 percent by weight and preferably having a relatively high content of novel stabilizer, for example, 5–15 percent by weight, is applied in a thin film (about 5–500 μm and preferably 10–100 μm) to a shaped article made from a polymer containing little or no ultraviolet stabilizers. Such composition may be applied at the same time as the shaping of the base structure, for example by coextrusion. Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20 percent, preferably about 1 to about 15 percent and most preferably about 2 to about 10 percent by weight of the outer layer composition, of at least one of the benzotriazole compounds of the present invention.

British Patent Appn. No. 2,290,745 describes a number of methods have been developed to concentrate UV absorbers near or at the surface of polymeric materials. These include surface impregnation (see U.S. Pat. Nos. 3,309,220, 3,043,709, 4,481,664 and 4,937,026) and coating a plastic article with solutions containing thermoplastic resins and UV absorbers (see U.S. Pat. Nos. 4,668,588 and 4,353,965). Both techniques suffer from drawbacks including requiring additional processing steps (i.e. applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner in known coextrusion equipment as taught in U.S. Pat. Nos. 3,487,505 and 3,557, 265. Coextrusion is a well recognized method of producing laminated thermoplastic materials by simultaneously extruding various numbers of layers which form a single composite material. U.S. Pat. No. 4,540,623 describes coextruded materials of at least forty layers. Other methods produce as few as two or three different layers.

In one embodiment, the invention also relates to thermoplastic articles coated with a thermoplastic layer 0.1 to 10 mil (0.00254 mm to 0.254 mm), preferable 0.1 to 5 mil (0.00254 mm to 0.127 mm), thick, in which said layer contains 0.1% to 20% by weight of benzotriazole compounds herein. Preferred concentrations of are 2% to 15% by weight; most preferred concentrations of 5% to 10% by weight.

The benzotriazole compounds of the instant invention may be incorporated into the thermoplastics of the surfaces layer by standard methods such as dry mixing the additives with granular resin prior to extruding.

The benzotriazole layer may be applied to one or both sides of the thermoplastic article.

Laminated thermoplastic articles corresponding to the present invention which contain additional layers such as a water resistant layer as found in U.S. Pat. No. 4,992,322 are also within the scope of the present invention.

The core layer and the coating layer may be of the same thermoplastic resin or different thermoplastic polyesters, polyester carbonates, polyphenylene oxide, polyvinyl chloride, polypropylene, polypropylene, polyethylene, polyacrylates, polymethacrylates and copolymers and blends such as styrene and acrylonitrile on polybutadiene and styrene with maleic anhydride.

The polymers stabilized in this way are notable for high weathering resistance, especially for high resistance to UV light. This enables them to retain their mechanical properties and their color and gloss for a long time even when used outside. Moreover, due to the bondable nature of the presently claimed benzotriazole compounds, migration of these UV absorbs between the layers of the multi-layer coatings is minimized.

In another embodiment of the present invention, the novel mixtures comprising at least one benzotriazole can be used as stabilizers for coatings, for example for paints. Of particular interest are coatings and paints for the automobile industry. The invention therefore also relates to those compositions which are film-forming binders for coatings.

Such novel coating compositions comprise about 0.01 to about 20 percent, preferably about 0.01 to about 10 percent and more preferably about 0.02 to about 5 percent by weight of the binder of the coating composition of the presently claimed benzotriazoles of the present invention.

Multilayer systems are possible here as well, where the concentration of the novel stabilizer in the outer layer can be relatively high, for example from about 0.01 to about 20 percent, preferably about 0.01 to about 10 percent, and more preferably about 0.02 to about 5 percent by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates.

The binder can in principle be any binder which is customary in industry, for example those described in Ullmann's Encyclopedia of Industrial Chemistry, 5th Edition, Vol. A18, pp. 368–426, VCH, Weinheim 1991, which is incorporated herein by reference. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Such binders can be a cold-curable or hot-curable binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991, which is incorporated herein by reference. Preferred binders include those which comprise a functional acrylate resin and a crosslinking agent.

A wide variety of binders may be employed in such coating systems. Examples of suitable coating compositions containing specific binders include but are not limited to:
1. paints based on cold- or hot-cross-linkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyan
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;

7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;
11. paint systems based on siloxane-modified or fluorine-modified acrylate resins.

In addition to the binder and novel benzotriazoles of the present invention, the coating composition according to the invention preferably further comprise an additional ultraviolet light absorber or stabilizer, including but not limited to those specifically listed above. The additional stabilizer/absorber is employed in an amount of about 0.01 to about 5 percent, preferably about 0.02 to about 2 percent by weight of the binder.

The ultraviolet light stabilizer mixtures may include terically hindered amines and/or 2-hydroxyphenyl-2H-benzotriazoles. The stabilizer may be a 2,2,6,6-tetraalkylpiperidine compound containing at least one group of the formula

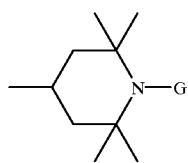

in which G is hydrogen or methyl, especially hydrogen.

Examples of additional preferred tetraalkylpiperidine compounds which can be used as an additional ultraviolet stabilizer are given in EP-A-356 677, pages 3–17, sections a) to f). These sections of this EP-A are incorporated herein by reference as part of the present description. It is particularly preferred to employ the following tetraalkylpiperidine compounds:

bis(2,2,6,6-tetramethylpiperid-4-yl)succinate,
bis(2,2,6,6-tetramethylpiperid-4-yl)sebacate,
bis(1,2,2,6,6-pentamethylpiperid-4-yl)sebacate,
di(1,2,2,6,6-pentamethylpiperid-4-yl)butyl-(3,5-di-tert-butyl-4-hydroxybenzyl)malonate,
bis(1-octyloxy-2,2,6,6-tetramethylpiperid-4-yl)sebacate,
tetra(2,2,6,6-tetramethylpiperid-4-yl)butane-1,2,3,4-tetracarboxylate,
tetra(1,2,2,6,6-pentamethylpiperid-4-yl)butane-1,2,3,4-tetracarboxylate,
2,2,4,4-tetramethyl-7-oxa-3,20-diaza-21-oxo-dispiro[5.1.11.2]heneicosane,
8-acetyl-3-dodecyl-1,3,8-triaza-7,7,9,9-tetramethylspiro[4.5]decane-2,4-dione, or a compound of the formulae

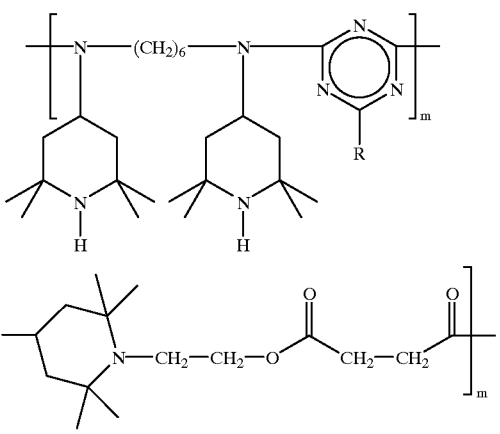

in which m is 5–50.

In addition to the binder, the benzotriazoles and additional ultraviolet stabilizer/absorber, the coating composition can also comprise further components such as but not limited to solvents, pigments, dyes, plasticizers, stabilizers, thixotropic agents, drying catalysts and/or leveling agents. Examples of possible components are those described in Ullmann's Encyclopedia of Industrial Chemistry, 5th Edition, Vol. A18, pp. 429–471, VCH, Weinheim 1991, which is incorporated herein by reference.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metal Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the abovementioned publication Ullmann's Encyclopedia of Industrial Chemistry, 5th Edition, Vol. A18, pages 451–453, which is incorporated herein by reference. In radiation-curable coating compositions, the novel stabilizers can also be employed with or without the addition of additional UV light stabilizers, including sterically hindered amines.

The coating compositions according to the invention can be applied to any desired substrates, for example to metal, wood, plastic or ceramic materials. They are preferably used as topcoats in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by conventional methods, for example by brushing, spraying, pouring, dipping or electrophoresis; see also Ullmann's Encyclopedia of Industrial Chemistry, 5th Edition, Vol. A18, pp. 491–500 which is incorporated herein by reference.

Depending on the binder system, the coatings can be cured at room temperature or may require heating. The coatings are preferably cured at about 50 to about 150° C., and in the case of powder coatings, even at higher temperatures.

The coatings obtained in accordance with the invention have excellent resistance to the damaging effects of light, oxygen and heat. In particular, the presently claimed coatings provide good light stability and weathering resistance.

The invention therefore also relates to a coating, in particular a paint, which has been stabilized against the damaging effects of light, oxygen and heat by a content of the benzotriazole compounds of the present invention. The paint may be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented base coat that is in adhesion to the primer, and which comprises a film-forming binder and an organic pigment or dye, an inorganic pigment, a metallic pigment, or a mixture thereof; and a clear top coat that is in adhesion to the base coat, and which comprises a film-forming binder and optionally a transparent pigment. The paint is preferably a topcoat for automobiles.

The invention furthermore relates to a process for stabilizing a coating based on organic polymers against damage by light, oxygen and/or heat, which comprises mixing with the coating composition a mixture comprising benzotriazole compounds of the present invention, as well as the use of mixtures comprising the benzotriazoles of the present invention in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The benzotriazoles of this invention may be applied topically by polishing a surface with a compositions comprising the benzotriazoles and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics, and wood.

The present invention is further directed towards the use of the novel benzotriazoles of the present invention in photographic materials as stabilizer against damage by light, especially by UV light.

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel benzotriazoles can be combined with other UV absorbers, especially those which are dispersible in aqueous gelatin, for example with hydroxyphenylbenzotriazoles (such as those disclosed, for example, in U.S. Pat. No. 4,853,471, U.S. Pat. No. 4,973,702, U.S. Pat. No. 4,921,966 and U.S. Pat. No. 4,973,701 all of which are incorporated herein by reference), benzophenones, oxanilides, cyanoacrylates, salicylates, or acrylonitriles or thiazolines. In this context it is advantageous to employ these additional, oil-dissolved UV absorbers in the photographic material in layers other than those comprising the novel benzotriazole UV absorbers.

In particular, it is possible successfully to stabilize photographic materials similar to those described in U.S. Pat. No. 4,518,686.

The invention therefore additionally relates to a photographic material comprising, on a support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a benzotriazole of the present invention.

It is preferred that in photographic materials which have a layer comprising a benzotriazole, that such layer is disposed above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, wherein a benzotriazole of the present invention must be present at least in one layer.

The photographic material preferably has gelatin interlayers between the silver-halide emulsion layers. It is also preferred that photographic materials in which the silver halide in the blue-sensitive, green-sensitive and/or red-sensitive layer is silver chloride bromide which comprises at least 90 mol % of silver chloride.

The novel benzotriazole employed in photographic materials can be incorporated, alone or together with the color coupler and, if used, additional additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids, and also alkylamides and phenols.

Preferred color couplers for use in the compositions of the invention, examples of such compounds, further additives such as color cast inhibitors, DIR couplers and further light stabilizers, such as UV absorbers, phenols, phosphorus compounds, organometallic complexes, hydroquinones and hydroquinone ethers, and more precise details on the structure of various photographic materials are well known in the art and can be found, for example, in the publications EP-A-531 258 and EP-A-520 938, and in the literature cited therein all of which is incorporated herein by reference.

Additionally, the novel benzotriazoles are suitable for the photochemical stabilization of undyed, dyed or printed fiber materials. Examples of such fiber materials include but are not limited to silk, leather, wool, polyamide or polyurethanes, and cellulose-containing fiber materials of all kinds. Examples of such fiber materials are the natural cellulose fibers, such as cotton, linen, jute and hemp, and also viscose staple fiber and regenerated cellulose. Preferred textile fiber materials are those of cotton.

The novel benzotriazoles are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with the novel compound offer to the human skin.

To this end, a benzotriazole of the present invention is applied to the textile fiber material by one of the customary dyeing methods in a quantity of about 0.01 to about 5 percent, preferably about 0.1 to about 3 percent and more preferably about 0.25 to about 2 percent by weight of the fiber material.

The novel benzotriazoles can be applied to the fiber material in various ways and fixed on the fiber, especially in the form of aqueous dispersions or printing pastes.

The textile fiber materials finished with the benzotriazole possess improved protection against photochemical breakdown of the fiber and yellowing phenomena, and, in the case of dyed fibre material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with the presently claimed benzotriazole has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with at least one of the benzotriazoles of the present invention are permeable to UV radiation. The determination of the sun protection factor of textile fiber materials is explained, for example, in WO 94/04515 or in J. Soc. Cosmet. Chem. 40, 127–133 (1989) and can be carried out analogously thereto.

Additionally, the UV absorbers according to the invention are suitable as photoprotective agents in cosmetic preparations. The invention additionally relates, therefore, to a cosmetic preparation comprising at least one benzotriazole of the present invention and cosmetically acceptable carriers or auxiliaries.

The novel cosmetic composition contains from about 0.1 to about 15 percent, preferably from about 0.5 to about 10 percent by weight of the cosmetic composition of the presently claimed benzotriazole and a cosmetically acceptable auxiliary.

The cosmetic composition can be prepared by physically mixing at least one benzotriazole of the present invention with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50 percent of an oily phase, from 5 to 20 percent of an emulsifier and from 30 to 90 percent water. The oil phase mentioned can comprise any oil which is suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employed emulsifier, for example one or more ethoxylated esters of naturally ccurring compounds, for example polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

The following examples further illustrate the various embodiments of the present invention. They are not to be construed as limiting the claims in any manner.

EXAMPLES

Example 1

A solution of 95% nitrosylsulfuric acid (1.88 g, 14.0 mmol) in sulfuric acid (3.3 g) was added to a solution of 2-nitroaniline (1.93 g, 14.0 mmol) in a mixture of acetic acid (23 ml) and propionic acid (9 ml) at 0–5° C. A solution of 2,2'-dihydroxy-5,5'-di-tert-octyl-biphenyl (1.44 g, 3.51 mmol, obtained from Enzymol International, Inc., Columbus, Ohio) in pyridine (6.0 ml) was then added over a period of 15 minutes at 0–5° C. After warming to 20° C., ammonium sulfate (21.0 g, 159 mmol) was added and the reaction mixture was heated to 40° C. for 8 hours. The mixture was then poured into water (100 ml) and extracted with methylene chloride (100 ml). The combined extracts were washed with water to a pH of 6, dried over anhydrous magnesium sulfate, and concentrated in vacuo to give a crude product (2.46 g) comprising 3,3'-bis-(2-nitrophenylazo)-5,5-di-tert-octyl-1,1'-biphenyl-2,2'-diol and 3-(2-nitrophenylazo)-5,5'-di-tert-octyl-1,1'-biphenyl-2,2'-diol. The bis- and the mono-azo compounds were separated as described below:

A sample of the crude product prepared by the above procedure (3.80 g) was chromatographed on a silica gel (160 g packed in a column) eluting with a mixture of acetic acid, toluene and hexanes. The initial composition of the solvent mixture was 0.5/25/74.5 (acetic acid/toluene/hexane) and it was followed by a sequence of progressively more polar solvent mixtures having the following compositions: 0.5/40/59.5; 0.5/50/49.5; 0.5/60/39.5; and 0.5/70/29.5 to give;

FRACTION A: 3,3'-bis-(2-nitrophenylazo)-5,5'-di-tert-octyl-1,1'-biphenyl-2,2'-diol (0.33 g), characterized by $^1$H and $^{13}$C nuclear magnetic resonance spectroscopy (NMR) and high resolution electron impact mass spectroscopy (HREI/MS): m/e=Found:708.3646; Calculated: 708.3635;

FRACTION B: An unresolved mixture containing 3,3'-bis-(2-nitrophenylazo)-5,5'-di-tert-octyl-1,1'-biphenyl-2,2'-diol and 3-(2-nitrophenylazo)-5,5'-di-tert-octyl-1,1'-biphenyl-2,2'-diol eluted between the pure fractions, FRACTION A and FRACTION C (1.25 g).

FRACTION C: 3-(2-nitrophenylazo)-5,5'-di-tert-octyl-1,1'-biphenyl-2,2'-diol (0.26 g), characterized by $^1$H and $^{13}$C Nuclear magnetic resonance spectroscopy (NMR) and high resolution electron impact mass spectroscopy (HREI/MS): m/e=Found: 559.3412; Calculated: 559.3410.

Example 2

3,3'-bis-(2H-benzotriazol-2-yl)-5'-di-tert-octyl-1,1'-biphenyl-2,2'-diol (COMPOUND 1)

Zinc powder (0.424 g) was added to a solution containing a mixture of 3,3'-bis-(2-nitrophenylazo)-5,5'-di-tert-octyl-1,1'-biphenyl-2,2'-diol and 3-(2-nitrophenylazo)-5,5'-di-tert-octyl-1,1'-biphenyl-2,2'-diol (FRACTION B in EXAMPLE 1) prepared by the method described in EXAMPLE 1 (0.70 g), 3 molar aqueous sodium hydroxide (0.54 ml), and a 9:1 mixture of toluene and isopropanol (7 ml) at 60° C. over a period of 2 hours with stirring. An additional amount of 3 molar aqueous sodium hydroxide (0.54 ml) was then added. The temperature was then raised to 75° C. and stirring was continued for 6 hours. After addition of toluene and water, the pH was adjusted to 6 with hydrochloric acid and the layers separated. The toluene layer was washed successively with 1% hydrochloric acid, 10% phosphoric acid, and 5% sodium bicarbonate and after adding activated charcoal (Darco KB-B), clay (Clay 22), and diatomaceous earth, it was stirred and thereafter filtered. The solvent was removed under reduced pressure to give a mixture of 3,3'-bis-(2H-benzotriazol-2-yl)-5,5'-di-tert-octyl-1,1'-biphenyl-2,2'-diol and 3-(2H-benzotriazol-2-yl)-5,5'-di-tert-octyl-1,1'-biphenyl-2,2'-diol (0.49 g). The bis- and the mono-benzotriazoles were separated as described below:

A sample of the crude product prepared by the above procedure (0.49 9) was filtered through silica gel (20 g packed in a column) and eluted with ethyl acetate. The solvent was removed and replaced with hexanes. The resulting solution was chromatographed by radial thin layer chromatography eluting with a mixture of acetic acid, ethyl acetate, and toluene (0.5/25/74.5). The solvent was then removed and the resulting solid was triturated with hexanes to give:

PRODUCT A: 3,3'-bis-(2H-benzotriazol-2-yl)-5,5'-di-tert-octyl-1,1'-biphenyl-2,2'-diol (COMPOUND 1) (0.033 g), characterized by $^1$H nuclear magnetic resonance spectroscopy (NMR), ultraviolet and mass spectroscopy; $\lambda_{max}$(toluene): 310 and 353 nm; $\epsilon_{310}$=25,600; $\epsilon_{353}$=28,300; high resolution electron impact mass spectroscopy (HREI/MS): m/e=Found: 644.3815; Calculated: 644.3839; and PRODUCT B: 3-(2H-Benzotriazol-2-yl)-5,5'-di-tert-octyl-1,1'-biphenyl-2,2'-diol (0.144 g), characterized by $^1$H nuclear magnetic resonance spectroscopy (NMR), ultraviolet spectroscopy, and mass spectroscopy; $\lambda_{max}$(toluene): 332 nm; $\epsilon_{332}$=15,400; high resolution electron impact mass spectroscopy (HREI/MS): m/e=Found: 527.3498; Calculated: 527.3512.

Example 3

3,3'-bis-(2H-benzotriazol-2-yl)-5,5'-di-tert-butyl-1,1'-biphenyl-2,2'-diol (COMPOUND 2)

A solution of sodium nitrite (7.0 g) in water (18 ml) was added dropwise to a cold (0° C.) solution of 2-nitroaniline (13.8 g) in concentrated hydrochloric acid (50 ml) while maintaining the temperature at 0–5° C. After stirring for 30 minutes, water was added until the reaction mixture became clear. The resulting solution was then added dropwise to a solution of 2,2'-dihydroxy-5,5'-di-tert-butyl-biphenyl (10.0 g, prepared by oxidatively dimerizing 2,4-di-tert-butyl phenol by the method described in Annal., Vol. 645, page 25(1961) and thereafter debutylating the tert-butyl group ortho- to the hydroxy group by the procedure described in Org. Prep. Proced. Int., Vol. 6, No. 3, page 117(1974), water (300 ml), 10% aqueous sodium hydroxide, and methanol (200 ml) over a period of 60 minutes at 0 to 5° C. After warming slowly to 25° C. and stirring at that temperature for an additional 60 minutes, the product was collected by suction filtration, washed and air dried to give 3,3'-bis-(2-nitrophenylazo)-5,5'-di-tert-butyl-1,1'-biphenyl-2,2'-diol.

A mixture of the 3,3'-bis-(2-nitrophenylazo)-5,5'-di-tert-butyl-1,1'-biphenyl-2,2'-diol (3.5 g), zinc powder (6.38 g), 15% aqueous sodium hydroxide (20 ml), and ethanol (40 ml)

was boiled under reflux in a nitrogen atmosphere for three hours. The hot mixture was filtered over diatomaceous earth. After cooling in an ice bath and acidification with hydrochloric acid, the precipitated product was collected by suction filtration, washed with water and air dried. Purification of the crude product by dry column chromatography using a mixture of hexane and ethyl acetate (9:1 v/v) as the eluent gave pure 3,3'-bis-(2H-benzotriazol-2-yl)-5,5'-di-tert-butyl-1,1'-biphenyl-2,2'-diol (COMPOUND 2) (0.8 g); m.p. 234° C.

Example 4

3,3'-bis-(2H-benzotriazol-2-yl)-5,5'-di-tert-butyl-1, 1'-biphenyl-2,2'-diol (COMPOUND 2)

Anhydrous ferric chloride (6.44 g, 0.038 mol) was added over a period of 30 minutes to a methylene chloride (300 ml) solution of 2-(2H-benzotriazol-2-yl)-4-tert-butyl-phenol (5.3 g, 0.019 mol) known as TINUVIN® PS Light Stabilizer, a product of CIBA SPECIALTIES, Hawthorne, N.Y. The resulting mixture was stirred at room temperature for 6 hours. After filtering over diatomaceous earth, the filtrate was extracted with dilute hydrochloric acid, washed with water and dried. Evaporation of the solvent gave 3,3'bis-(2H-benzotriazol-2-yl)-5,5'-di-tert-butyl-1,1'-biphenyl-2,2'-diol (COMPOUND 2) as a white powder; m.p. 234° C.

Example 5

3,3'-bis-(2H-benzotriazol-2-yl)-5,5'-di-cumyl-1,1'-biphenyl-2,2'-diol (COMPOUND 3)

Ortho-Nitroaniline (13.8 9) was added to concentrated hydrochloric acid (50 ml) and stirred at 50° C. for 30 minutes. The white suspension was cooled to 0° C. and a solution of sodium nitrite (7.0 g) in water (18 ml) was added dropwise while maintaining a bath temperature at 0° C. to 5° C. After stirring for 30 minutes, sufficient water was added to obtain a clear solution.

The clear solution was added dropwise over a period of 30 minutes to a solution of para-cumyl phenol (21.2 g) in a mixture of 10% aqueous sodium hydroxide (300 ml) and methanol (360 ml) at 0° C. with stirring. After stirring for an hour, acetic acid (40 ml) was added and after stirring for an additional 15 minutes, the crude azo compound was filtered, washed with ice cold water and methanol and dried under a reduced pressure.

Zinc powder was added in portions to the azo compound (15 g) suspended in a mixture of ethanol (125 ml) and 2 Normal aqueous sodium hydroxide heated under reflux. After continued heating (3 hours), the reaction mixture was filtered while hot over diatomaceous earth and after cooling in an ice bath acidified with dilute hydrochloric acid. The precipitate was collected by suction filtration, washed with cold water and air dried to give 2-(2H-benzotriazol-2-yl)-4-cumyl-phenol (1.2 g); m.p. 119–121° C.

Anhydrous ferric chloride (2.6 g) was added over a period of 30 minutes to a solution of 2-(2H-benzotriazol-2-yl)-4-cumyl-phenol (2.7 g) in methylene chloride (100 ml) and the resulting mixture stirred at room temperature for 6 hours. After filtering over celite, the filtrate was extracted with dilute hydrochloric acid, washed with water and purified by column chromatography using hexane/ethyl acetate 9:1 v/v mixture as the eluent. Evaporation of the volatiles gave 3,3'bis-(2H-benzotriazol-2-yl)-5,5'-di-cumyl-1,1'-biphenyl-2,2'-diol (COMPOUND 3) as a white powder, m.p. 249–251° C.

Example 6

3,3'-bis-(2H-benzotriazol-2-yl)-5,5'-di-methyl-1,1'-biphenyl-2,2'-diol (COMPOUND 4)

Anhydrous ferric chloride (21.6 g, 130 mmol) was added over a period of 120 minutes to a solution of 1-(2H-benzotriazol-2-yl)-4-methylphenol, (15.0 g, 66.6 mmol), a product of CIBA SPECIALTIES, Hawthorne, N.Y., under the tradename TINUVIN P Light Stabilizer, in a mixture of methylene chloride (700 mL), mixed hexanes (20 mL) and water 200 mg). After the addition was complete, the resulting mixture was stirred at room temperature for 36 hours. The resulting suspension was diluted with 500 mL of methylene chloride and shaken with 700 mL of 5% HCl. The mixture was filtered and the filter cake washed further with several portions of 5% HCl, followed by several portions of water, methanol, and finally, methylene chloride. Vacuum oven drying of the resulting solid gave 14.2 g (95% yield) of a greyish-yellow powder, mp>300° C. Recrystallization from o-dichlorobenzene gave 3,3'-bis-(2H-benzotrialzol-2-yl)-5,5'-di-methyl-1,1'-biphenyl-2,2'-diol (COMPOUND 4) as light yellow needles $^1$H NMR (300 MHz, DMSO-$d_8$+7% 2M NaOH) δ 7.82 (m, 4H), 7.32 (m, 4H), 7.10 (m, 2H), 6.82 (m, 2H), 2.17 (s, 3H).

Example 7

3,3'-bis(2H-benzotriazol-2-yl)-5,5'-di-tert-octyl-1,1'-biphenyl-2,2'-diol (COMPOUND 1)

Anhydrous ferric chloride (0.2 g, 32.1 mmol) was added over a period of 120 minutes to a solution of 2-(2H-benzotriazol-2-yl)-4-tert-octylphenol (5.2 g, 16.1 mmol), CYASORB® UV-5411 Light Stabilizer, and water (63.5 mg) in methylene chloride (52 mL), and the resulting mixture was stirred at room temperature for 18 hours. HPLC analysis of the reaction mixture (detector wavelength=290 nm) indicated 40 area % of product and 51 area % of starting material. After filtering over celite, the filtrate was extracted with dilute hydrochloric acid, the organic layer washed with water, and dried. Evaporation of the solvent gave a crude product which was extracted with acetone to remove any unreacted starting material. Recrystallization from ethyl acetate gave 3,3'-bis-(2H-benzotriazol-2-yl)-5,5'-di-tert-octyl-1,1'-biphenyl-2,2'-diol (COMPOUND 1) as a white powder (24% yield), m.p. 209–211° C.

Example 7A 3,3'-bis-(2H-benzotriazol-2-yl)-5,5'-di-tert-octyl-1,1'-biphenyl-2,2'-diol (synthesis with mixed solvent, low temperature)

Anhydrous ferric chloride (5.25 g, 32.5 mmol) was added over a period of 120 minutes to a solution of 2-(2H-benzotriazol-2-yl)-4-tert-octylphenol, (5.15 g, 15.9 mmol), CYASORB® UV-5411 Light Stabilizer, in a mixture of methylene chloride (52 mL), mixed hexanes (55 mL) and water (60 mg) at 0° C. After the addition was complete, the resulting mixture was removed from the cooling bath and stirred at room temperature for 18 hours. HPLC analysis of the reaction mixture (detector wavelength=290 nm) indicated 54.5 area % of COMPOUND 1 and 41.9 area % of starting material.

Example 8

3,3'-bis-(2H-benzotriazol-2-yl)-1,1'-biphenyl-2,2'-diol (COMPOUND 5) (See Scheme I).

Anhydrous ferric chloride (53.5 g, 0.33 mol) was added over a period of 180 minutes to a solution of 2-(2H-benzotriazol-2-yl)phenol, (20.0 g, 94.7 mmol), prepared by the method of Rosevear and Wilshire (Scheme I), Aust. J. Chem. 1985, 38, 1163–76, in methylene chloride (200 mL) and water (160 mg) at 0° C. After the addition was complete, the resulting mixture was removed from the cooling bath and stirred at room temperature for 36 hours. HPLC analysis of the reaction mixture (detector wavelength=290 nm) indicated 87 area % of product and 13 area % of starting material. The mixture was diluted with 2 L of methylene chloride and extracted with two 500 mL portions of 5% HCl, and two 1 L portions of water. The organic layer was rotary evaporated, leaving 19.4 g of a light grey solid which was 90% pure to HPLC. Surprisingly, very little or none of the para coupled product was found, as confirmed by NMR analysis. Recrystallization from o-dichlorobenzene gave COMPOUND 5 as off-white needles. $^1$H NMR (300 MHz, CD$_2$Cl$_2$) δ 11.62 (s, 2H), 8.41 (d, 2H), 7.88 (m, 4H), 7.42 (m, 4H), 7.39 (m, 2H), 7.10 (t, 2H).

Scheme I

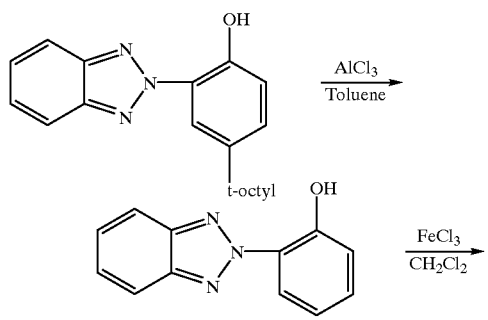

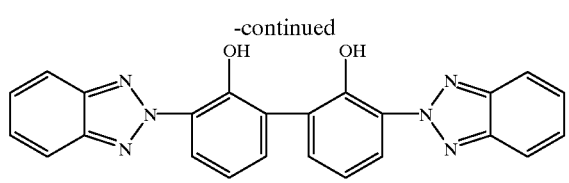

Example 9

Studies of the Ferric Chloride Reaction

Table 1 shows a summary of ferric chloride reaction results. The area % values of UV-5411 and COMPOUND 1 are given at 290 nm. The putative impurities arising from UV-5411 and COMPOUND 1 (based on MS results) are also given in area %. In all cases ferric chloride was weighed in a glove box with a nitrogen atmosphere.

The reaction (as determined by HPLC) was carried out (0.09% water (by weight relative to total reaction weight) in methylene chloride, with 35% added hexanes), with a reaction temperature of 39° C. instead of the usual room temperature. The area % value for COMPOUND 1 that resulted was 38% versus 49% for the best case. However, when the reaction was cooled to 0° C. for the duration of the ferric chloride addition, the area % value which resulted was 54.5%. In this case the impurities formed were minimized relative to the room temperature reaction. Also since the same lot of Aldrich ferric chloride had been used with all added-water experiments, an Acros lot of ferric chloride was used in the reaction (entry 4). As seen in the table, virtually identical results were observed, showing good reproducibility across these two lots. Before water addition was known to be important, a large yield variability had been seen between these same two lots.

As can be observed in Table 1, yields are improved by the addition of water and hexanes, running the reaction at low temperature, and the addition of greater than two equivalents of ferric chloride (although in the latter case decomposition competes with further conversion).

TABLE 1

FeCl$_3$-Based Bis-benzotriazole Synthesis
(HPLC Area %, 290 nm, 17 h reaction)

| Entry | Reaction Unless otherwise noted 2.0 molar equivalents of Aldrich FeCl$_3$ were used. | Cyasorb ® 5411 | Cyasorb ® 5411 impurities | COMPOUND 1 | Bisbenzo-triazole impurities |
|---|---|---|---|---|---|
| 1 | FeCl$_3$/CH$_2$Cl$_2$ | 72.2 | 1.4 | 16.8 | 9.6 |
| 2 | FeCl$_3$/CH$_2$Cl$_2$/0.09% H$_2$O | 51.3 | 1 | 40.4 | 7.2 |
| 3 | FeCl$_3$/CH$_2$Cl$_2$/35% hexane/0.09% H$_2$O | 45.6 | 0.9 | 49.1 | 4.4 |
| 4 | FeCl$_3$/CH$_2$Cl$_2$/35% hexane/0.09% H$_2$O Acros FeCl$_3$ | 44.2 | 1.2 | 49.8 | 4.6 |
| 5 | FeCl$_3$/CH$_2$Cl$_2$/35% hexane/0.09% H$_2$O 0° C. during 2 hour addition | 41.9 | 0.7 | 54.5 | 2.9 |

TABLE 1-continued

FeCl₃-Based Bis-benzotriazole Synthesis
(HPLC Area %, 290 nm, 17 h reaction

| Entry | Reaction Unless otherwise noted 2.0 molar equivalents of Aldrich FeCl₃ were used. | Cyasorb ® 5411 | Cyasorb ® 5411 impurities | COMPOUND 1 | Bisbenzo-triazole impurities |
|---|---|---|---|---|---|
| 6 | FeCl₃/CH₂Cl₂/35% hexane/0.09% H₂O 2.5 eq. FeCl₃ | 38.4 | 2.3 | 52.1 | 7.2 |
| 7 | FeCl₃/CH₂Cl₂/35% hexane/0.09% H₂O 38° C. during 2 hour addition | 59.5 | <0.5 | 37.9 | 2.5 |
| 8 | FeCl₃/CH₂Cl₂/35% hexane/0.09% H₂O 4.0 eq. FeCl₃ | 35.4 | 6.6 | 45.9 | 12.1 |
| 9 | FeCl₃/CH₂Cl₂/35% hexane/0.09% H₂O 0° C. over 7 h, 3.0 equivalents FeCl₃ | 27.9 | 6.3 | 51.3 | 14.3 |

Several other reactions were run, varying the concentration and solvent. In the reaction when a 10% UV-5411 in $CH_2Cl_2$/hexanes concentration was used (the highest concentration used previously was 5%) analysis showed the same area % at ½ hour conversion (48%) as the 5% case.

Three reactions were performed in 30% naphtha/toluene to assess the feasibility of eliminating methylene chloride from the process. A previous reaction run in pure toluene had given 17.4 area % of COMPOUND 1. The first reaction was run with a 7% UV-5411 concentration at room temperature, and 0.07% added water. A 29.6 area % of COMPOUND 1 resulted (see Entry 1, Table 2 below). The second experiment was run at 0° C. during the ferric chloride addition. As entry 2 in the table shows, addition of ferric chloride at low temperature causes a slight increase in conversion to product. This phenomenon was also noted in the methylene chloride process. A more concentrated reaction mixture (Entry 3 in the table) does not appear to be detrimental.

TABLE 2

FeCl₃-Based Bis-Benzotriazole Synthesis
(HPLC Area %, 290 nm, 17 h reaction)

| Entry | Reaction | Cyasorb ® UV-5411 | Cyasorb ® UV-5411 impurities | COMPOUND 1 | Bis-benzo-triazole im-purities |
|---|---|---|---|---|---|
| 1 | FeCl₃/Naphtha/ Tol/0.07% H₂O 7% UV-5411 Concentration | 52.2 | 1.7 | 29.6 | 14.4 |
| 2 | FeCl₃/Naphtha/ Tol/0.07% H₂O 7% UV-5411 Concentration 0° C | 50.6 | 1.5 | 33 | 12.2 |
| 3 | FeCl₃/Naphtha/ Tol/0.07% H₂O 14% UV-5411 Concentration | 54.4 | 1.5 | 30.5 | 13.2 |

Example 10

Stabilization of Polypropylene with Bis-Benzotriazoles

The performance of COMPOUND 1 prepared by the method of EXAMPLE 7 was evaluated. The polypropylene films were prepared by: (1) blending in methylene chloride a mixture of COMPOUND 1 (0.5 wt %), IRGANOX® 1010 Antioxidant (0.10 wt %), distearylthiodipropionate (0.25 wt %), calcium stearate (0.10 wt %), and PROFAX® 6301 polypropylene from HIMONT Corporation, (2) extruding the blend in a Brabender extruder using a 4:1 screw at 60 RPM speed, with zone 1, zone 2, and zone 3 temperatures at 200° C., (3) pulling through a water bath, (4) drying, (5) pelletizing, and (6) compression moulding into a 0.0127 mm (0.5 mil) film. The films were irradiated in an Xenon Arc Weatherometer (Atlas Model CI 65) at a black panel temperature of 63.5° C., relative humidity of 50%, using a cycle of 102 minutes of light followed by 18 minutes of both light and deionized water spray. Samples, in triplicate, were removed weekly and the rate of photooxidation was determined using an infrared spectrometer by following the carbonyl absorption at 1715 cm$^{-1}$. Failure endpoints were determined by measuring the "CARBONYL CHANGE" and "COMPLETE LOSS OF PHYSICAL PROPERTIES" endpoints. The Carbonyl Change endpoint was determined by measuring the time required for a 0.5 change in the carbonyl absorption intensity. The Complete Loss of Physical Properties endpoint was determined by flexing a sample and recording cracking of the sample upon flexing. The results are summarized in TABLE 3.

TABLE 3

STABILIZATION OF POLYPROPYLENE
WITH BIS-BENZOTRIAZOLES

|  | (%) | 0.5 Carbonyl Change (Hours) | Complete Loss of Physical Properties (Hours) |
|---|---|---|---|
| COMPOUND 1 | 0.5 | 900 | 1030 |
| Control (No Stabilizer) | — | 140 | 140 |

Example 11

Stabilization of Polycarbonate with Bis-Benzotriazoles

The performance of COMPOUNDS 1 and 5 was evaluated in comparison to the control (no stabilizer) and to various commercial benzotriazole UV absorbers. For this example, the crude sample of COMPOUND 5 was not recrystallized from o-dichlorobenzene, but was purified as follows. Volatiles were removed at 200° C. and 1 mm pressure, and the residue dissolved in tetrahydrofuran to form a 0.3% solution of the additive in the solvent. The solution was decolorized with Amberlyst-15 ion exchange resin and after filtration of the resin, the solution was concentrated to a 2% solids level. COMPOUND 5 was recovered as a light yellow solid after filtration. Polycarbonate plaques were prepared by: (1) dry blending the additives at 0.35 weight % with GE Lexan 121–112 polycarbonate, (2) extruding the blend in a Haake torque rheometer base using a 0.75 inch 25:1 single screw extruder—4 zone, single pass, at 50–55 RPM speed, with zone 1, zone 2, zone 3, and zone 4 temperatures at 260, 260, 265 and 265° C., respectively, (3) pulling through a water bath, (4) drying, (5) pelletizing, (6) redrying at 120° C. for 4–48 hours in a forced air oven, (7) injection molding in an Arburg "Allrounder" hydraulic injection molder (2×2.50× 0.100 inch plaques). Temperatures used were as follows: nozzle 275° C.; nozzle side, 279° C., middle, 275° C., feed, 266° C; mold 95° C. The plaques were irradiated in a Xenon Arc Weatherometer as described by ASTM G-26 Standard using Test Method B with alternate exposure to light and darkness and an intermittent exposure to water spray maintaining an atmosphere temperature of 63±3° C. and a relative humidity of 30±5% (Miami, Fla. conditions). Failure endpoints were determined by measuring the number of hours of exposure necessary for an increase in 5 Yellowness Index (YI) units. The results are summarized in TABLE 4.

TABLE 4

STABILIZATION OF POLYCARBONATE
WITH BIS-BENZOTRIAZOLES

|  | Level (%) | Time to ΔYI = 5 (Hours) |
| --- | --- | --- |
| None | 0 | 167 |
| COMPOUND 1 | 0.35 | 1014 |
| Mixxim BB/100 ® | 0.35 | 1015 |
| Tinuvin ® 234 | 0.35 | 1023 |
| Eversorb ® 75 | 0.35 | 1121 |
| Cyasorb ® UV-5411 | 0.35 | 1170 |
| COMPOUND 5 | 0.35 | 1271 |

Mixxim BB/100 ® = 2,2'-Methyl [6-(2H-benzotriazol-2yl)] 4-tert-octylphenol, a product of Fairmount Chemical Co., Inc., Fairmount Newark, NJ
Tinuvin ® 234 = 2-(2H-Benzotriazol-2yl)-4,6-bis (α,α-dimethylbenzyl) phenol, a product of Ciba Specialty Chemicals, Ltd.
Eversorb ® 75 = 2-(2H-6-Chlorobenzotriazol-2-yl)-4,6-di-tert-butylphenol, a product of Everlight Chemical Industrial Corp., Everlight Chemical Industrial Corp., Taipei, Taiwan
Cyasorb ® UV-5411 = 2-(2H-Benzotriazol-2-yl)-4-tert-octylphenol, a product of Cytec Industries, Inc.

Example 12

Stabilization of Polycarbonate with Benzotriazoles

The performance of COMPOUNDS 1, 4, and 5 was evaluated in comparison to the control (no stabilizer) and to various commercially available benzotriazole UV absorbers. Polycarbonate plaques were prepared by: (1) dry blending the additives at 0.35 weight % with GE Lexan 105 polycarbonate, with 0.1% of added Mark 2112 phosphite; (2) extruding the blend in a Haake torque rheometer base using a 0.75 inch 25:1 single screw extruder -4 zone, single pass, at 50–65 RPM speed, with zoe 1, zone 2, zone 3, and zone 4 temperatures at 265, 265, 270 and 275° C., respectively; (3) pulling through a water bath; (4) drying; (5) pelletizing; (6) redrying at 120° C. for 4–48 hours in a forced air oven; (7) injection molding in an Arburg 'Allrounder' hydraulic injection molder (2×2.50×100 plaques). Temperatures used were as follows: nozzle, 275° C.; nozzle side, 280° C.; middle, 275° C.; feed, 266° C.; mold, 95° C. The plaques were irradiated in a Xenon Arc Weathermeter as described by ASTM G-26 Standard using Test Method B with alternate exposure to light and darkness and an intermittent exposure to water spray maintaining an atmosphere temperature of 63±30° C. and a relative humidity of 30±5% (Miami, Fla. conditions). Failure endpoints were determined by measuring the number of hours of exposure necessary for the Yellowness Index (Y1) value to reach 14 units. The results are summarized in TABLE 5.

TABLE 5

STABILIZATION OF POLYCARBONATE WITH
BENZOTRIAZOLES

|  | Level (%) | Time to Y1 = 14 (Hours) |
| --- | --- | --- |
| None | 0 | 247 |
| ADK STAB LA-31 | 0.35 | 1345 |
| Tinuvin ® 234 | 0.35 | 1420 |
| COMPOUND 4 | 0.35 | 1430 |
| COMPOUND 1 | 0.35 | 1435 |
| COMPOUND 5 | 0.35 | 1554 |
| Cyasorb ® UV-5411 | 0.35 | 1592 |

LA-31 ® = ADK STAB LA-31 ® 2,2'-Methylenedi [Bis-2-benzotriazolyl)-4-tert-octylphenol, a product of Asahi Denka Kogyo K.K., Tokyo, Japan
Tinuvin ® 234 = 2-(2H-Benzotriazol-2-yl)-4,6-bis (α,α-dimethylbenzyl) phenol, a product of Ciba Specialty Chemicals (HK), Ltd.
Cyasorb ® UV-5411 = 2-(2H-Benzotriazol-2-yl)-4-tert-octylphenol, a product of Cytec Industries, Inc.

Example 13

Stabilization of Coatings With Benzotriazoles

COMPOUND 1 was formulated in a clear acrylic melamine coatings which were applied to aluminum panels for accelerated weathering testing as follows. COMPOUND 1 (2% based on total resin solids) was pre-dissolved in xylenes, alone and in combination with Sanduvor® 3058 HALS (0.5% or 1.0% based on total resin solids), and added to the clear acrylic melamine formulation given in Table 6. A formulation containing Tinuvin® 328 (2% based on total resin solids) was also prepared for comparison purposes. Unpolished aluminum panels, measuring 4"×12", obtained from ACT Laboratories, Inc. (Hillsdale, Mich.) were coated with the clear coat formulation of Table 6. The draw-down technique, using WC-52 Wire-Cators™ (Leneta co., Ho-Ho-Kus, N.J.), was used to apply the clear coats to the panels. Coatings 2 mil thick were obtained. The clear coats were allowed to flash for 10 min. at ambient temperature and cured for 30 min. at 135° C.

TABLE 6

ACRYLIC MELAMINE CLEAR COAT FORMULATION

| Material | Amount |
| --- | --- |
| Joncryl ® 510 acrylic resin (80%) | 81.25 g |
| Cymel ® 303 cross-linker | 35.0 g |
| Cycat ® | 1.0 g |
| n-Butanol | 20.0 g |
| Xylene | 16.0 g |
| COMPOUND 1 | 0.326 g |

TABLE 6-continued

ACRYLIC MELAMINE CLEAR COAT FORMULATION

| Material | Amount |
| --- | --- |
| Sanduvor ® 3058[b] | 0.0816/0.163 g |
| Joncryl - SC Johnson Wax, Inc. Racine, WI | |

[a]2% based on total resin solids
[b]Optional - when utilized the amount is 0.5 or 1.0% based on total resin solids Accelerated weathering was carried out with a QUV device equipped with UVA-340 fluorescent bulb. The weathering protocol was based on ASTM G53 (GM cycle), which is which is weathering under alternate cycles of (i) UV light at 70° C. for 8 hours and (ii) condensation with no UV light at 50° C. for 4 hr. Specular properties (gloss and distinctness of image, or DOI) were measured as a function of weathering time.

The effectiveness of COMPOUND 1 on surface properties is summarized in tables 7 (gloss retention) and 8 (distinctness of image retention (DOI)). Tables 7 and 8 also illustrate the added gloss and DOI protection obtained by supplementing with HALS, Sanduvor® 3058.

TABLE 7

QUV WEATHERING (UVA-340 BULBS) OF AN ACRYLIC MELAMINE CLEAR COAT STABILIZED WITH COMPOUND 1, EFFECT ON GLOSS RETENTION

| | Hours Exposure | | | | | |
| --- | --- | --- | --- | --- | --- | --- |
| Stabilizer | 1000 | 2055 | 2967 | 4136 | 6172 | 7176 |
| None | 86 | 70 | 62 | —[a] | — | — |
| 2% Tinuvin ® 328 | 85 | 63 | 52 | 37 | 19[b] | — |
| 2% COMPOUND 1 | 95 | 79 | 70 | 59 | 34 | 27 |
| 2% COMPOUND 1 0.5% Sanduvor ® 3058 | 100 | 96 | 91 | 84 | 64 | 53 |
| COMPOUND 1 1.0% Sanduvor ® 3058 | 99 | 95 | 89 | 84 | 70 | 62 |

[a]Panel removed after 3488 hr. due to delamination.
[b]Panel removed due to delamination.

TABLE 8

QUV WEATHERING (UVA-340 BULBS) OF AN ACRYLIC MELAMINE CLEAR COAT STABILIZED WITH COMPOUND 1, EFFECT ON DOI RETENTION

| | Hours Exposure | | | | | |
| --- | --- | --- | --- | --- | --- | --- |
| Stabilizer | 1000 | 2055 | 2967 | 4136 | 6172 | 7176 |
| None | 88 | 77 | 77 | —[a] | — | — |
| 2% Tinuvin ® 328 | 67 | 43 | 31 | 24 | 12[b] | — |
| 2% COMPOUND 1 | 91 | 67 | 60 | 50 | 20 | 20 |
| 2% COMPOUND 1, 0.5% Sanduvor ® 3058 | 100 | 89 | 79 | 68 | 48 | 39 |
| COMPOUND 1, 1.0% Sanduvor ® 3058 | 100 | 93 | 84 | 79 | 52 | 48 |

[a]Panel removed after 3488 hr. due to delamination.
[b]Panel removed due to delamination.

Example 14

The coatings of Example 13 were weathered on an Atlas Ci65 WeatherOmeter equipped with xenon arc lamps using the SAE J1960 automotive exterior test protocol. The effectiveness COMPOUND 1 is given in Tables 9 (gloss retention) and 10 (Delta E). These data also illustrate the added benefit of combining with HALS, Sanduvor® 3058.

TABLE 9

XENON WEATHERING (SAE J1960 AUTOMOTIVE EXTERIOR) OF AN ACRYLIC MELAMINE COATING STABILIZED WITH COMPOUND 1, EFFECT ON PERCENT GLOSS RETENTION

| | Hours Exposure | | | | |
| --- | --- | --- | --- | --- | --- |
| Stabilizer | 999 | 1995 | 3900 | 4383 | 4838 |
| None | 90 | 33 | —[a] | — | — |
| 2% Tinuvin ® 328 | 93 | 86 | 43 | 24 | 23 |
| 2% COMPOUND 1 | 96 | 91 | 54 | 50 | 38 |
| 2% COMPOUND 1, 0.5% Sanduvor ® 3058 | 97 | 91 | 79 | 68 | 49 |
| 2% COMPOUND 1, 1.0% Sanduvor ® 3058 | 96 | 92 | 83 | 79 | 74 |

[a]Panel removed after 2493 hr. due to delamination.

TABLE 10

XENON WEATHERING (SAE J1960 AUTOMOTIVE EXTERIOR) OF AN ACRYLIC MELAMINE COATING STABILIZED WITH COMPOUND 1, EFFECT ON DELTA E

| | Hours Exposure | | |
| --- | --- | --- | --- |
| Stabilizer | 999 | 1995 | 4383 |
| None | 2.00 | 1.75 | —[a] |
| 2% Tinuvin ® 328 | 1.00 | 1.15 | 1.27 |
| 2% COMPOUND 1 | 0.69 | 0.58 | 0.82 |
| 2% COMPOUND 1, 0.5% Sanduvor ® 3058 | 0.69 | 0.38 | 0.37 |
| 2% COMPOUND 1, 1.0% Sanduvor ® 3058 | 0.48 | 0.66 | 0.45 |

[a]Panel removed after 2493 hr. due to delamination. Delta E was 5.07.

Example 15

The coatings of Example 13 were weathered in Miami, Fla. The testing was performed in accordance with ASTM G7-89 at a tilt angle of 5° C. from the horizontal facing south with specimens mounted unbacked. As can be seen from Table 11, COMPOUND 1 and Tinuvin® 328 were comparable efficiency in reducing total color change (delta E) relative to the unstabilized coating.

TABLE 11

FLORIDA WEATHERING (5° SOUTH, DIRECT) OF AN ACRYLIC MELAMINE COATING STABILIZED WITH COMPOUND 1, EFFECT ON DELTA E

| | Exposure Time (months) | | |
| --- | --- | --- | --- |
| Stabilizer | 3 | 6 | 12 |
| None | 3.10 | 3.93 | 4.81 |
| 2% Tinuvin ® 328 | 0.56 | 0.80 | 0.75 |
| 2% COMPOUND 1 | 0.54 | 0.75 | 0.79 |
| 2% COMPOUND 1, 0.5% Sanduvor ® 3058 | 0.37 | 0.55 | 0.49 |
| 2% COMPOUND 1, 1.0% Sanduvor ® 3058 | 0.24 | 0.30 | 0.31 |

Example 16

Stabilization of a Multilayer Polycarbonate Article with Bis-benzotriazoles

The performance of Compounds 1 and 5 was evaluated in comparison to the control (no stabilizer) and to two commercial benzotriazole UV stabilizers in a polycarbonate thin film molded to an unstabilized polycarbonate plaque. The films were prepared by (1) dry blending the additives at 7 wt. % with Lexan 105 virgin flake and 0.1% Mark 2112 phosphite, (2) extruding the blend in a Haake torque rheometer base equipped with a 0.75 inch 25:1 single mixing screw extruder—4 zone, single pass at 55–65 rpm speed, with zone 1, zone 2, zone 3, and zone 4 temperatures at 246, 265, 295, and 304° C., respectively, (3) pulling through a water bath, (4) drying, (5) pelletizing, (6) redrying at 120° C. for 4–48 hours in a forced air oven, and (7) compression molding from PC compounded pellets into 2 mil films at 300° C. using a 30 second dwell hold without pressure, 30-second dwell hold with 35K pressure. Plaques without benzotriazole were prepared using an Arburg 'Allrounder' hydraulic injection molder (2×2.5×0.100" plaques). Temperatures used were as follows: nozzle 275° C.; nozzle side 280° C; middle 275° C; feed 266° C., (2) cutting plaques to fit mold as needed, (3) laying capstock film over plaque evenly, (4) sandwiching between foil sheets and steel plates, (5) placing onto press plate and apply immediate pressure to 35 k psi for 3 seconds only (6) removing sample and cool with ice or air. The laminated sample plaques were exposed in the xenon-arc weatherometer as determined by ASTM G-26 Standard using Test Method B with alternate exposure to light and darkness and an intermittent exposure to water spray maintaining an atmosphere temperature of 63°±3° C. and a relative humidity of 30±5% (Miami, Fla. conditions). Color (YI) was determined with a Macbeth Color Eye Colorimeter under Lab conditions with illuminate C, 2° observer, specular component excluded, and UV component included. The results are summarized in Table 12 below

TABLE 12

Stabilization of a Multilayer Polycarbonate Article with Bis-benzotriazoles

| | Level | Time to YI = 9 |
|---|---|---|
| None | 0 | ?? |
| LA-31 | 7.0 | 1510 |
| Compound 1 | 7.0 | 1765 |
| Compound 5 | 7.0 | 2205 |
| UV-5411 | 7.0 | >2500 |

We claim:

1. A composition of matter comprising a benzotriazole compound selected from the group consisting of a 3-(2H-benzotriazol-2-yl)-1,1'-biphenyl-2,2'-diol, a 3,3'-bis-(2H-benzotriazol-2-yl)-1,1'-biphenyl-2,2'-diol and a mixture thereof, wherein the 3-(2H-benzotriazol-2-yl)-1,1'-biphenyl-2,2'-diol compound is represented by the formula:

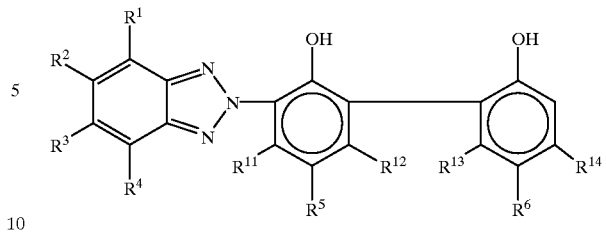

wherein $R^1$, $R^2$, $R^3$ and $R^4$ are the same or different and each is independently carboxy; cyano; halogen; or hydrogen; or linear, branched, or cyclic alkyl, alkenyl, aralkyl, acyl, alkoxy, alkoxyalkyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted; and $R^5$, $R^6$, $R^{11}$, $R^{12}$, $R^{13}$ and $R^{14}$ are the same or different and each is independently carboxy; cyano; halogen; or hydrogen; or linear, branched, or cyclic alkyl, alkenyl, aralkyl, acyl, alkoxy, alkoxyalkyl, alkyl carboxylic acid, alkyl ester, alkyl sulfone, alkyl sulfoxide, amido, amino, aryl, aryl sulfone, aryl sulfoxide, polyether, thioalkyl or thioaryloxy which may be substituted or unsubstituted, with the proviso that a hydroxy group is ortho- to a benzotriazole moiety; and the 3,3'-bis-(2H-benzotriazol-2-yl)-1,1'-biphenyl-2,2'-diol compound is represented by the formula:

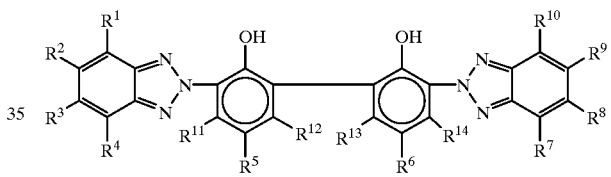

wherein $R^1$, $R^2$, $R^3$, $R^4$, $R^5$, $R^6$, $R^{11}$, $R^{12}$, $R^{13}$ and $R^{14}$ are as described above, and $R^7$, $R^8$, $R^9$ and $R^{10}$ the same or different and each is independently carboxy; cyano; halogen; or hydrogen; or linear, branched, or cyclic alkyl, alkenyl, aralkyl, acyl, alkoxy, alkoxyalkyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted; and with the proviso that each hydroxy group is ortho- to a benzotriazole moiety.

2. The composition of claim 1 wherein the bis-(2H-benzotriazol-2-yl)-biaryldiol compound is represented by the formula:

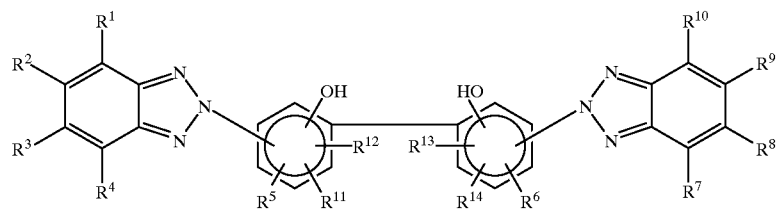

wherein
  $R^1$, $R^2$, $R^3$, $R^4$, $R^7$, $R^8$, $R^9$, and $R^{10}$ are the same or different and each is independently carboxy; cyano; halogen; or hydrogen; or linear, branched, or cyclic alkyl, alkenyl, aralkyl, acyl, alkoxy, alkoxyalkyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted with the proviso that each hydroxy group is ortho- to a benzotriazole moiety; and
  $R^5$, $R^6$, $R^{11}$, $R^{12}$, $R^{13}$ and $R^{14}$ are the same or different and each is independently carboxy; cyano; halogen; or hydrogen; or linear, branched, or cyclic alkyl, alkenyl, aralkyl, acyl, alkoxy, alkoxyalkyl, alkoxycarbonyl, alkoxycarbonylalkyl, alkyl carboxylic acid, alkyl ester, alkyl sulfone, alkyl sulfoxide, amido, amino, aryl, aryl sulfone, aryl sulfoxide, polyether, thioalkyl or thioaryloxy which may be substituted or unsubstituted with the proviso that each hydroxy group is ortho- to a benzotriazole moiety.

3. The composition of claim 1 wherein $R^5$ and $R^6$ are —$CH_3$, —$C_2H_5$, n-$C_3H_7$, i-$C_3H_7$, n-$C_4H_9$, s-$C_4H_9$, t-$C_4H_9$, —$C_8H_{17}$, —$CH(C_2H_5)C_5H_{11}$, t-$C_8H_{17}$, —$C_9H_{18}$, -Ph, —$C(CH_3)_2Ph$, —$C(CH_3)_2C_2H_5$, —$CH_2C(CH_3)_3$, —COOH, —$C(O)OC_8H_{17}$, —$C_2H_4COOH$, —$C_2H_4CONH_2$, —$C_2H_4COOCH_3$, —$C_2H_4COOCH_2CH_2OH$, —$CH_2CH_2OH$, —$C_2H_4COOCH_2CH_2OC(O)C(CH_3)CH_2$, —$C_2H_4COOC_8H_{17}$, —$C_2H_4COOCH(C_2H_5)C_5H_{11}$, —$C_2H_4COO(C_2H_4O)_8H$, —$C_2H_4COOCH_2CH(OH)CH_2OC(O)C(CH_3)CH_2$ or —$C_2H_4COOCH(CH_2OH)CH_2OC(O)C(CH_3)CH_2$ and $R^3$ is chloro, methoxy, thiophenoxy, phenyl sulfoxide, phenyl sulfone, —$SC_8H_{17}$, —$SC_{13}H_{27}$, —$S(O)C_{12}H_{25}$ or —$S(O)_2C_{12}H_{25}$.

4. The composition of claim 1 wherein $R^5$ and $R^6$ are the same or different and each is independently is hydrogen or alkyl of 1 to 18 carbon atoms or aralkyl of 7 to 18 carbon atoms and wherein the remaining R groups are all hydrogen.

5. The composition of claim 4 wherein $R^5$ and $R^6$ are the same and are cumyl, hydrogen, methyl, tert-butyl or tert-octyl.

6. The composition of claim 5 wherein $R^5$ and $R^6$ are hydrogen.

7. The composition of claim 5 wherein $R^5$ and $R^6$ are methyl.

8. The composition of claim 1 wherein the mole ratio of the 3,3'-bis-(2H-benzotriazol-2-yl)-1,1'-biphenyl-2,2'-diol to 3-(2H-benzotriazol-2-yl)-1,1'-biphenyl-2,2'-diol is from about 99:1 to about 1:1.

9. A composition of matter wherein the azo compound is a 3-(2-nitroarylazo)-1,1'-biaryl-2,2'-diol, a 3,3'-bis-(2-nitroarylazo)-1,1'-biaryl-2,2'-diol or a mixture thereof, wherein the 3-(2-nitroarylazo)-1,1'-biaryl-2,2'-diol is represented by the formula:

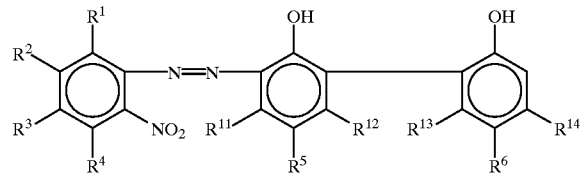

wherein $R^1$, $R^2$, $R^3$, $R^4$, $R^5$, $R^6$, $R^{11}$, $R^{12}$, $R^{13}$ and $R^{14}$ are the same or different and each is independently cyano; halogen; or hydrogen; or linear, branched, or cyclic alkyl, alkenyl, aralkyl, acyl, alkoxy, alkoxyalkyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted.

10. The composition of claim 9 wherein $R^5$ and $R^6$ are H, —$CH_3$, —$C_2H_5$, n-$C_3H_7$, i-$C_3H_7$, n-$C_4H_9$, s-$C_4H_9$, t-$C_4H_9$, —$C_8H_{17}$, —$CH(C_2H_5)C_5H_{11}$, t-$C_8H_{17}$, —$C_9H_{18}$, -Ph, —$C(CH_3)_2Ph$, —$C(CH_3)_2C_2H_5$, —$CH_2C(CH_3)_3$, —COOH, —$C(O)OC_8H_{17}$, —$C_3H_6OH$, —$C_2H_4COOH$, —$C_2H_4CONH_2$, —$C_2H_4COOCH_3$, —$C_2H_4COOCH_2CH_2OH$, —$CH_2CH_2OH$, —$C_2H_4COOCH_2CH_2OC(O)C(CH_3)CH_2$, —$C_2H_4COOC_8H_{17}$, —$C_2H_4COOCH(C_2H_5)C_5H_{11}$, —$C_2H_4COO(C_2H_4O)_8H$, —$C_2H_4COOCH_2CH(OH)CH_2OC(O)C(CH_3)CH_2$ or —$C_2H_4COOCH(CH_2OH)CH_2OC(O)C(CH_3)CH_2$ and $R^3$ is chloro, methoxy, thiophenoxy, phenyl sulfoxide, phenyl sulfone, —$SC_8H_{17}$, —$SC_{13}H_{27}$, —$S(O)C_{12}H_{25}$ or —$S(O)_2C_{12}H_{25}$.

11. The composition of claim 9 wherein $R^5$ and $R^6$ are the same or different and each is independently of hydrogen or alkyl of 1 to 18 carbon atoms or aralkyl of 7 to 18 carbon atoms; and wherein the remaining R groups are all hydrogen.

12. The composition of claim 11 wherein $R^5$ and $R^6$ are the same and are cumyl, hydrogen, methyl, tert-butyl, or tert-octyl.

13. The composition of claim 12 wherein $R^5$ and $R^6$ are the same and are hydrogen.

14. The composition of claim 12 wherein $R^5$ and $R^6$ are the same and are methyl.

15. The composition of claim 9 wherein the 3,3'-bis-(2-nitroarylazo)-1,1'-biaryl-2,2'-diol is represented by the formula:

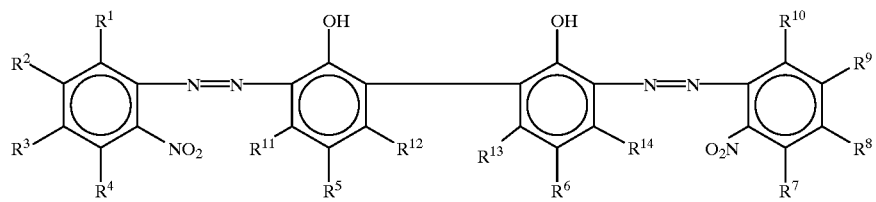

wherein $R^1$, $R^2$, $R^3$, $R^4$, $R^5$, $R^6$, $R^7$, $R^8$, $R^9$, $R^{10}$, $R^{11}$, $R^{12}$, $R^{12}$, $R^{13}$ and $R^{14}$ are the same or different and each is independently cyano; halogen; or hydrogen; or linear, branched, or cyclic alkyl, alkenyl, aralkyl, acyl, alkoxy, alkoxyalkyl, alkoxycarbonylalkyl, alkyl carboxylic acid, alkyl ester, alkyl sulfone, alkyl sulfoxide, amido, amino, aryl, aryl sulfone, aryl sulfoxide, hydroxyalkyl, hydroxyalkyloxy, polyether, thioalkyl or thioaryloxy which may be substituted or unsubstituted.

16. The composition of claim 15 wherein $R^5$ and $R^6$ are H, —$CH_3$, —$C_2H_5$, n-$C_3H_7$, i-$C_3H_7$, n-$C_4H_9$, s-$C_4H_9$, t-$C_4H_9$, —$C_8H_{17}$, —$CH(C_2H_5)C_5H_{11}$, t-$C_8H_{17}$, —$C_9H_{18}$, -Ph, —$C(CH_3)_2$Ph, —$C(CH_3)_2C_2H_5$, —$CH_2C(CH_3)_3$, —COOH, —$C(O)OC_8H_{17}$, —$C_3H_6OH$, —$C_2H_4COOH$, —$C_2H_4CONH_2$, —$C_2H_4COOCH_3$, —$C_2H_4COOCH_2CH_2OH$, —$CH_2CH_2OH$, —$C_2H_4COOCH_2CH_2OC(O)C(CH_3)CH_2$, —$C_2H_4COOC_8H_{17}$, —$C_2H_4COOCH(C_2H_5)C_5H_{11}$, —$C_2H_4COO(C_2H_4O)_8H$, —$C_2H_4COOCH_2CH(OH)CH_2OC(O)C(CH_3)CH_2$ or —$C_2H_4COOCH(CH_2OH)CH_2OC(O)C(CH_3)CH_2$ and $R^3$ is chloro, methoxy, thiophenoxy, phenyl sulfoxide, phenyl sulfone, —$SC_8H_{17}$, —$SC_{13}H_{27}$, —$S(O)C_{12}H_{25}$ or —$S(O)_2C_{12}H_{25}$.

17. The composition of claim 15 wherein $R^5$ and $R^6$ are the same or different and each is hydrogen or alkyl of 1 to 18 carbon atoms or aralkyl of 7 to 18 carbon atoms; and wherein the remaining R groups are all hydrogen.

18. The composition of claim 17 wherein $R^5$ and $R^6$ are the same and are cumyl, hydrogen, methyl, tert-butyl, or tert-octyl.

19. The composition of claim 18 wherein $R^5$ and $R^6$ are the same and are hydrogen.

20. The composition of claim 18 wherein $R^5$ and $R^6$ are the same and are methyl.

21. The composition of claim 9 wherein the mole ratio of 3,3'-bis-(2-nitroarylazo)-1,1'-biaryl-2,2'-diol to 3-(2-nitroarylazo)-1,1'-biaryl-2,2'-diol is from about 99:1 to about 1:1.

22. A degradation stable composition, comprising;
    (i) a degradable polymer; and
    (ii) a stabilizingly effective amount of a composition according to claim 1.

23. The composition of claim 22 wherein the degradable polymer is selected from the group consisting of polyethylene, polypropylene, polystyrene, polyacrylate, polyurethane, polyamide, amino-resin-crosslinked polymer mixtures, physical blends, copolymers and terpolymers thereof, polyolefins, polyesters, polyethers, polyketones, polyamides, polyurethanes, polystyrenes, polyacrylates, polyacetals, polyacrylonitriles, polybutadienes, ABS, SAN (styrene acrylonitrile), ASA (acrylate styrene acrylonitrile), cellulosic acetate butyrate, cellulosic polymers, polyimides, polyamideimides, polyetherimides, polyphenylsulfide, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers of amines or blocked amines with activated unsaturated and/or methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

24. The composition of claim 22 wherein the degradable polymer is a polycarbonate or polycarbonate blend.

25. The composition of claim 22 wherein the degradable polymer is an amino-crosslinked thermoset acrylic or polyester.

26. The composition of claim 22 wherein the degradable polymer is an polyisocyanate-crosslinked acrylate or polyester.

27. The degradable stable composition of claim 22 wherein the degradable polymer further comprises a polymerization or cross-linking catalyst.

28. The composition of claim 22 wherein the bis-(2H-benzotriazole-2-yl) biaryldiol compound is selected from the group consisting of a 3-(2H-benzotriazol-2-yl)-5,5'-di-tert-octyl-1,1'biphenyl-2,2'diol, a 3,3'-bis-(2H-benzotriazol-2-yl)-5,5'-di-tert-octyl-1,1'-biphenyl-2,2'-diol, an N-oxide thereof and a mixture thereof.

29. The composition of claim 22 wherein the benzotriazole compound is 3,3'-bis-(2H-benzotriazol-2-yl)-1,1'-biphenyl-2,2'-diol.

30. A multi-layer degradation stable composition, comprising:
    (i) a first portion which comprise a degradable polymer substantially free of ultraviolet stabilizers; and
    (ii) a second portion which comprises a degradable polymer and stabilizingly effective amount of a composition according to claim 1.

31. The multi-layer degradation stable composition of claim 30 wherein the amount of benzotriazole compound in the second layer is from about 0.1 to about 20%.

32. The multi-layer degradation stable composition of claim 30 wherein the amount of benzotriazole compound in the second layer is from about 1 to about 15%.

33. The multi-layer degradation stable composition of claim 30 wherein the amount of benzotriazole compound in the second layer is from about 2 to about 10%.

34. A method of stabilizing a degradable polymer, said method comprising:
    adding to said degradable polymer a composition according to claim 1.

35. The method of claim 34 wherein the degradable polymer is selected from the group consisting of polycarbonate, polyethylene, polypropylene, polystyrene, polyacrylate, polyurethane, polyamide, amino-resin-crosslinked polymer mixtures, physical blends, copolymers and terpolymers thereof, polyolefins, polyesters, polyethers, polyketones, polyamides, polyurethanes, polystyrenes, polyacrylates, polyacetals, polyacrylonitriles, polybutadienes, ABS, SAN (styrene acrylonitrile), ASA (acrylate styrene acrylonitrile), cellulosic acetate butyrate, cellulosic polymers, polyimides, polyamideimides, polyetherimides, polyphenylsulfide, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates,carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers of amines or blocked amines with activated unsaturated and/or methylene compounds, ketimines with activated unsaturated and methylene compounds, polyketimines in combination with unsaturated acrylic polyacetoacetate resins/polyketimines in combination with unsaturated acrylic resins, radiation curable compositions, epoxymelamine resins, organic dyes, cosmetic products, cellulose-based paper formulations, photographic film paper, ink, and blends thereof.

36. The method of claim 34 wherein the degradable polymer is a polycarbonate or polycarbonate blend.

37. The method of claim 34 wherein the degradable polymer is an amino-crosslinked thermoset acrylic or polyester.

38. The method of claim 34 wherein the degradable polymer is an polyisocyanate-crosslinked acrylate or polyester.

39. The method of claim 35 wherein the benzotriazole compound is selected from the group consisting of a 3-(2H-benzotriazol-2-yl)-5,5'-di-tert-octyl-1,1'biphenyl-2,2'diol, a 3,3'-bis-(2H-benzotriazol-2-yl)-5,5'-di-tert-octyl-1,1'-biphenyl-2,2'-diol, an N-oxide thereof and a mixture thereof.

* * * * *

UNITED STATES PATENT AND TRADEMARK OFFICE
CERTIFICATE OF CORRECTION

PATENT NO. : 6,344,505 B1  Page 1 of 1
DATED : February 5, 2002
INVENTOR(S) : Valentine, Jr. et al.

It is certified that error appears in the above-identified patent and that said Letters Patent is hereby corrected as shown below:

Title page,
Inventors add, -- Dennis J. Jakiela, Orange, CT. --

Signed and Sealed this

Twenty-third Day of April, 2002

Attest:

JAMES E. ROGAN
*Attesting Officer*   *Director of the United States Patent and Trademark Office*